US011177041B1

(12) United States Patent
Sutton et al.

(10) Patent No.: US 11,177,041 B1
(45) Date of Patent: Nov. 16, 2021

(54) METHOD AND SYSTEM FOR CARDIAC RISK ASSESSMENT OF A PATIENT USING HISTORICAL AND REAL-TIME DATA

(71) Applicant: MedAmerica Data Services, LLC, Emeryville, CA (US)

(72) Inventors: Nathan Sutton, Pisgah Forest, NC (US); Justin Plumley, Durham, NC (US); Dipti Patel-Misra, Alamo, CA (US); Joshua Tamayo-Sarver, Los Gatos, CA (US)

(73) Assignee: MedAmerica Data Services, LLC, Emeryville, CA (US)

( * ) Notice: Subject to any disclaimer, the term of this patent is extended or adjusted under 35 U.S.C. 154(b) by 64 days.

(21) Appl. No.: 16/378,460

(22) Filed: Apr. 8, 2019

Related U.S. Application Data

(60) Provisional application No. 62/701,161, filed on Jul. 20, 2018.

(51) Int. Cl.
*G16H 50/30* (2018.01)
*G16H 10/60* (2018.01)
(Continued)

(52) U.S. Cl.
CPC ............ *G16H 50/30* (2018.01); *G16H 10/60* (2018.01); *G16H 50/70* (2018.01); *G16H 50/20* (2018.01)

(58) Field of Classification Search
CPC ........ G16H 10/60; G16H 50/20; G16H 50/70; G06N 20/00
See application file for complete search history.

(56) References Cited

U.S. PATENT DOCUMENTS

| 8,417,533 B2 | 4/2013 | Clawson |
| 9,092,964 B1 | 7/2015 | Chan et al. |

(Continued)

FOREIGN PATENT DOCUMENTS

| WO | 2014/042942 A1 | 3/2014 |
| WO | 2014/100736 A2 | 6/2014 |
| WO | 201/091603 A1 | 6/2017 |

OTHER PUBLICATIONS

VanHouten JP, et al. "Machine learning for risk prediction of acute coronary syndrome." AMIA Annu Symp Proc. 2014;2014:1940-1949. Published Nov. 14, 2014. (Year: 2014).*
(Continued)

*Primary Examiner* — Christopher L Gilligan
*Assistant Examiner* — Chance L Smith
(74) *Attorney, Agent, or Firm* — Mauriel Kapouytian Woods LLP; Elaine K. Lee; Michael Mauriel

(57) ABSTRACT

A method and system for assessing the risk of a cardiac event in a patient which utilizes real-time and historical data from Electronic Medical Record (EMR) systems is described. A risk of a cardiac event is estimated, in real-time or near-real-time, for a patient who is currently in a hospital emergency department. Batch data for one or more past patients is extracted from EMRs into a machine learning model. Using the machine learning model, a risk level for one or more past patients is calculated. A real-time database is constructed from streams of real-time Health Level 7 (HL7) clinical data, wherein at least one stream of real-time HL7 clinical data is associated with the current patient, and a risk prediction is estimated by joining the calculated risk level for the patient in the machine learning model with the real-time HL7 clinical data from the patient.

21 Claims, 8 Drawing Sheets

(51) Int. Cl.
   *G16H 50/70* (2018.01)
   *G16H 50/20* (2018.01)

(56) References Cited

U.S. PATENT DOCUMENTS

| | | |
|---|---|---|
| 9,177,106 B2 | 11/2015 | Smith et al. |
| 2004/0087864 A1 | 5/2004 | Grouse |
| 2008/0154642 A1 | 6/2008 | Marble et al. |
| 2008/0255885 A1 | 10/2008 | Eisenberger et al. |
| 2012/0029932 A1 | 2/2012 | Stein et al. |
| 2012/0215560 A1 | 8/2012 | Ofek et al. |
| 2012/0323588 A1 | 12/2012 | Kelly et al. |
| 2014/0236626 A1 | 8/2014 | Reddy Bynagari |
| 2014/0257122 A1* | 9/2014 | Ong ............... A61B 5/0468 600/515 |
| 2014/0297302 A1 | 10/2014 | Vanier et al. |
| 2015/0213224 A1 | 7/2015 | Amarasingham et al. |
| 2015/0287317 A1 | 10/2015 | Chan et al. |
| 2015/0339791 A1 | 11/2015 | Tetteh |
| 2016/0063209 A1 | 3/2016 | Malaviya |
| 2016/0364544 A1* | 12/2016 | Das ............... G16H 50/20 |
| 2017/0006135 A1 | 1/2017 | Siebel et al. |
| 2017/0091388 A1 | 3/2017 | Zolla et al. |
| 2017/0277732 A1 | 9/2017 | Dwire et al. |

OTHER PUBLICATIONS

Weiss, Jeremy C., et al. "Machine learning for personalized medicine: Predicting primary myocardial infarction from electronic health records." Ai Magazine 33.4 (2012): 33-45. (Year: 2012).*

Bhansali, V., et al., U.S. Appl. No. 16/297,456, entitled Real Time Parser for Use With Electronic Medical Records, filed Mar. 8, 2019.

Guillén, J., et al., U.S. Appl. No. 16/378,542, entitled Patient Callback Tool and Interface, filed Apr. 8, 2019.

Bhansali, V., et al., U.S. Appl. No. 16/378,439, entitled Patient Trackerboard Tool and Interface, filed Apr. 8, 2019.

Hsia, R.Y., et al., A National Study of the Prevalence of Life-Threatening Diagnoses in Patients with Chest Pain, Jul. 2016, pp. 1029-1032, vol. 176—No. 7, JAMA Internal Medicine.

Antman, E.M., et al., The TIMI Risk Score for Unstable Angina/Non-ST Elevation MI, A Method for Prognostication and Therapeutic Decision Making, American Medical Association, Aug. 16, 2000, pp. 835-842, vol. 284—No. 7, JAMA.

Lagerqvist, B., et al., FRISC score for selection of patients for an early invasive treatment strategy in unstable coronary artery disease, Interventional cardiology and surgery, Heart, 2005, pp. 1047-1052, vol. 91—Iss. 8, BMJ Journals.

Six, A.J., et al., Chest pain in the emergency room: value of the HEART score, Netherlands Heart Journal, Jun. 2008, pp. 191-196, vol. 16—No. 6.

Cervellin, G., et al., Diagnostic algorithms for acute coronary syndrome—is one better than another?, Annals of Translational Medicine, May 2016, 6 pages, vol. 4—No. 10.

Goodacre, S., et al., The health care burden of acute chest pain, Heart, 2005, pp. 229-230, 91(2).

Goodacre, S., et al., Cost effectiveness of diagnostic strategies for patients with acute, undifferentiated chest pain, Emergency Medicine Journal, 2003, pp. 429-433, 20(5).

Penumetsa, S.C., et al., Outcomes of Patients Admitted for Observation of Chest Pain, Archives of Internal Medicine, Jun. 11, 2012, pp. 873-877, vol. 172—No. 11.

Sharif, S., et al., Does This Patient With Chest Pain Have Acute Coronary Syndrome?, Annals of Emergency Medicine, Jul. 2017, pp. 44-45, vol. 70—No. 1.

Tang, E., et al., Global Registry of Acute Coronary Events (GRACE) hospital discharge risk score accurately predicts long-term mortality post acute coronary syndrome, American Heart Journal, Jan. 2007, pp. 29-35, vol. 153—No. 1, Elsevier.

Than, M., et al., What is an acceptable risk of major adverse cardiac event in chest pain patients soon after discharge from the Emergency Department? A clinical survey, International Journal of Cardiology, 2012, pp. 752-754, vol. 166—No. 3, Elsevier.

Rajkomar, A., et al., Scalable and accurate deep learning with electronic health records, Digital Medicine, May 8, 2018, pp. 1-10, vol. 1—No. 18, Nature Partner Journals.

* cited by examiner

ED Trackerboard List for May 31, 2517 13:20

| Patient Name | MRN | Encounter # | ED Arrival | ED Visits in 6 Mo | Last ED Visit | Attending Provider | Cardiac Predictive Risk | Predicted Outcome |
|---|---|---|---|---|---|---|---|---|
| Doe, John (72) | XYZ1234 | ABC12345 | 5/31/2517 13:04 | 4 | 4/30/2517 22:18 | Jones, Sarah | 75% (67% - 93%) | PCI |
| ... | ... | ... | ... | ... | ... | ... | ... | ... |
| ... | ... | ... | ... | ... | ... | ... | ... | ... |
| ... | ... | ... | ... | ... | ... | ... | ... | ... |
| Li, Jane (39) | XYZ1239 | ABD32112 | 5/31/2517 13:06 | 1 | 5/15/2517 18:25 | Yang, Cristina | 56% (24% - 85%) | AMI |
| ... | ... | ... | ... | ... | ... | ... | ... | ... |
| ... | ... | ... | ... | ... | ... | ... | ... | ... |
| ... | ... | ... | ... | ... | ... | ... | ... | ... |

Control Panel — All Sites

FIG. 6

METHOD AND SYSTEM FOR CARDIAC RISK ASSESSMENT OF A PATIENT USING HISTORICAL AND REAL-TIME DATA

CROSS REFERENCE TO RELATED APPLICATIONS

This application claims the benefit of priority to U.S. provisional application 62/701,161 filed Jul. 20, 2018. This and all other extrinsic materials discussed herein are incorporated by reference in their entirety.

BACKGROUND

The present technology relates generally to method and systems for assessing the risk of a cardiac event in a patient which utilize real-time and historical data from Electronic Medical Record (EMR) and Electronic Health Record (EHR) related systems. Herein, the term "EMR" is intended to include both EMR and EHR.

Herein, EMR data broadly includes, for example, data associated with medical or health care patients, data associated with medical or health conditions, status or situations, data associated with medical or health care, etc., whether such data is associated with particular medical or health topics or with individual patients.

Chest pain is one of the most common reasons for visit in an emergency department (ED). Even though only about 1 out of every 20 of the patients in the ED complaining of chest pain are diagnosed with acute coronary syndrome (ACS), many of these patients end up being admitted to the hospital because doctors generally would prefer to err on the side of caution and avoid discharging a patient that later experiences an acute myocardial infarction, or AMI. See Hsia, R. et al., "A National Study of the Prevalence of Life-Threatening Diagnoses in Patients with Chest Pain, JAMA Intern Med. 2016; 176(7):1029-1032. doi:10.1001/jamainternmed.2016.2498 (download available at jamanetwork.com/journals/jamainternalmedicine/fullarticle/2527387)

Patients presenting with unspecified chest pain in the emergency department (ED) are likely to hospitalized to undergo further observation and testing (Goodacre, 2005). Diagnostic tests such as cardiac biomarkers (Cervellin, Mattiuzzi, Bovo, & Lippi, 2016; Than et al., 2014) and stress tests (Penumetsa, Mallidi, Friderici, Hiser, & Rothberg, 2012) have a proven ability to rule-in patients with acute coronary syndrome, or ACS. A downside is that both the hospitalization of ED patients with unspecified chest pain and the diagnostic tests required to rule in ACS are costly endeavors (Goodacre & Calvert, 2003). In response, a variety of risk models such as the GRACE (Tang et al. 2007), FRISC (Lagerqvist, 2005), TIMI (Antman et al., 2000), and HEART (Six, Backus, & Kelder, 2008) scores have been developed to help rule-out the possibility of ACS and reduce the number of patients that require hospitalization for further testing. Unfortunately, these risk scores are not sufficiently sensitive to rule out the possibility of ACS at the time of ED presentation (Sharif & Upadhye, 2017).

Many research studies have been completed about these and other prior art risk models to help physicians diagnose or rule out the possibility of ACS. Full citations for the studies cited above and other research studies are provided below:

Antman, E. M., Cohen, M., Bernink, P. J. L. M., McCabe, C. H., Horacek, T., Papuchis, G., Braunwald, E. (2000). The TIMI Risk Score for Unstable Angina/Non-ST Elevation MI. Jama, 284(7), 835. doi.org/10.1001/jama.284.7.835

Lagerqvist, B. (2005). FRISC score for selection of patients for an early invasive treatment strategy in unstable coronary artery disease. Heart, 91(8), 1047-1052. doi.org/10.1136/hrt.2003.031369

Six, A. J., Backus, B. E., & Kelder, J. C. (2008). Chest pain in the emergency room: value of the HEART score. Netherlands Heart Journal, 16(6), 191-196. doi.org/10.1007/BF03086144

Cervellin, G., Mattiuzzi, C., Bovo, C., & Lippi, G. (2016). Diagnostic algorithms for acute coronary syndrome—is one better than another? Annals of Translational Medicine, 4(10), 193-193. doi.org/10.21037/atm.2016.05.16

Goodacre, S. (2005). The health care burden of acute chest pain. Heart, 91(2), 229-230. doi.org/10.1136/hrt.2003.027599

Goodacre, S., & Calvert, N. (2003). Cost effectiveness of diagnostic strategies for patients with acute, undifferentiated chest pain. Emergency Medicine Journal, 20(5), 429-433. doi.org/10.1136/emj.20.5.429

Penumetsa, S. C., Mallidi, J., Friderici, J. L., Hiser, W., & Rothberg, M. B. (2012). Outcomes of patients admitted for observation of chest pain. Archives of Internal Medicine, 172(11), 873-877. doi.org/10.1001/archinternmed.2012.940

Sharif, S., & Upadhye, S. (2017). Does This Patient With Chest Pain Have Acute Coronary Syndrome? Annals of Emergency Medicine, 70(1), 44-45. doi.org/10.1016/j.annemergmed.2016.09.039

Tang, E., Wong, C., and Herbison, P. Global Registry of Acute Coronary Events (GRACE) hospital discharge risk score accurately predicts long-term mortality post-acute coronary syndrome. American Heart Journal, 153(1), 29-35. doi.org/10.1016/j.ahj.2006.10.004

Than, M., Herbert, M., Flaws, D., Cullen, L., Hess, E., Hollander, J. E., Jaffe, A. (2018). What is an acceptable risk of major adverse cardiac event in chest pain patients soon after discharge from the Emergency Department? International Journal of Cardiology, 166(3), 752-754. doi.org/10.1016/j.ijcard.2012.09.171

One ongoing challenge for emergency department physicians is that they would like to be able to predict with some degree of accuracy which patients are not likely to experience acute myocardial infarction, so that they may safely discharge such patients home. Physicians tend to be risk averse when considering the discharge of patients presenting to the emergency department with unspecified chest pain and will generally only accept a missed diagnosis rate of around 1% (Than et al., 2018).

SUMMARY

Prior art tools described above such as the HEART score are not sufficient to accurately predict or identify acute coronary syndrome in the future. Instead, the HEART score recommends admission to the hospital or further expensive tests for around 30% of patients, leading to unnecessary hospitalizations and cardiac testing. Thus, physicians may, in the course of treating their patients with unspecified chest pain, err on the side of caution and order further hospitalization and testing rather than send the patient home and risk a missed diagnosis. The unneeded tests run in the emergency department as well as unnecessary admissions to hospitals for people who never experience an AMI are potentially avoidable costs in the current medical health care systems. A more accurate method of quickly determining the cardiac risk of patients presenting with chest pains in the ED would allow physicians and medical staff to focus their time and energy on the most at-risk patients.

Thus, a real-time or near real-time system is needed to provide emergency department physicians and other health care providers with an evidence-based, statistical evaluation about a patient's risk of AMI soon after the patient shows up to the emergency department.

Embodiments of the present invention provide a method and system for assessing the risk of a cardiac event in a patient which utilizes real-time and historical data from Electronic Medical Record (EMR) systems. A cardiac event risk is estimated in real-time or near real-time upon request by a clinician, such as an emergency department physician, for a patient who is currently in a hospital emergency department. Batch data for one or more past patients is extracted from EMRs of past patients into a machine learning model. Using the machine learning model, a risk level for one or more past patients is calculated. A real-time database is constructed from streams of real-time Health Level 7 (HL7) clinical data, wherein at least one stream of real-time HL7 clinical data is associated with the current patient, and a risk prediction is estimated by joining the calculated risk level for the patient in the machine learning model with the real-time HL7 clinical data from the patient.

The cardiac risk assessment tool in some embodiments of the present invention provides a data-driven model to address the shortcoming of rules-based models found in prior art by harnessing the power in both the depth and breadth in the electronic medical record. Some embodiments of the present invention allow physicians to more safely discharge low risk patients presenting with unspecified chest pain.

In some embodiments, the present invention incorporates a data model developed from the electronic medical record with thousands of covariates. In one embodiment of the present invention, there are 279 or more CCS categories, 271 or more prescription types, 476 or more types of surgeries, 25 or more major diagnosis categories, and 74 or more types of medical services in the data model. Taken together, these data represent a holistic view of a patient's history. In contrast, there are less than ten components for the GRACE, HEART, and TIMI scores.

In some embodiments, the present invention allows for scalability and increased accuracy in that the risk calculation utilizes a large number of data elements from the patient's medical record and also from the patient population as a whole, which is analyzed by a computer as opposed to a simple checklist for a physician. This offloading is necessary given the size and complexity of the problem, but it also allows physicians access to a much more flexible approximation of cardiac risk. In particular embodiments of the present invention, a cached architecture is used to deploy a batch process in real-time.

In some embodiments of the present invention, a cardiac risk assessment tool is developed based on a data-driven model utilizing data derived from historical and real-time events in the electronic medical record that is more effective at ruling-out ACS than the HEART score. With the goal of ruling-out ACS, the cardiac risk assessment tool utilized in one embodiment of the present invention had a missed diagnosis rate of 1.4% in a prospective validation of over 3,000 patients, which is equal to the stated risk tolerance of surveyed emergency physicians (Than et al., 2018). This and other embodiments of the present invention will help provide physicians with the evidence-based support they need when determining whether and/or when to discharge low risk patients who are presenting with unspecified chest pain from the ED.

BRIEF DESCRIPTION OF THE DRAWINGS

FIG. 6 illustrates a screenshot of an exemplary user interface display according to some embodiments of the invention;

Figure 1:
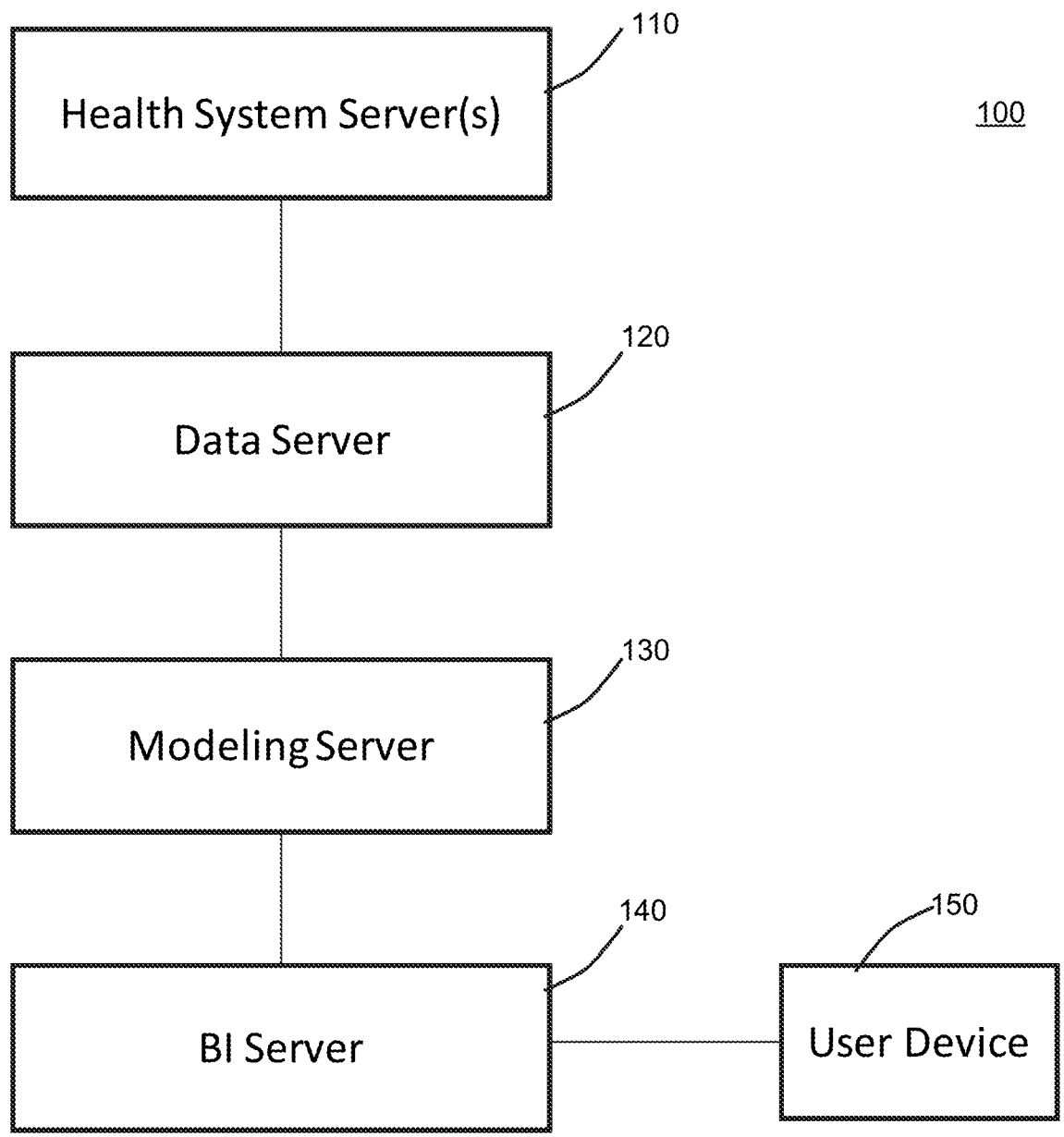
FIG. 1 illustrates a block diagram of an architecture of a system according to some embodiments of the invention.

While the invention is described with reference to the above drawings, the drawings are intended to be illustrative, and the invention contemplates other embodiments within the spirit of the invention.

DETAILED DESCRIPTION

The following description is presented to enable any person skilled in the art to make and use embodiments of the invention and is provided in the context of particular applications and their requirements. Various modifications to the exemplary embodiments will be readily apparent to those skilled in the art, and the generic principles defined herein may be applied to other embodiments and applications without departing from the spirit and scope of the invention. Thus, the present invention is not intended to be limited to the embodiments shown but is to be accorded the widest scope consistent with the principles and features disclosed herein.

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

Any process described in this application may be performed in any order and may omit any of the steps in the process. Processes may also be combined with other processes or steps of other processes.

FIG. 1 illustrates a block diagram of an architecture 100 of a system according to some embodiments of the invention. Depicted are one or more health system servers 110, a data server 120, a modeling server 130, a business intelligence (BI) server 140, and an exemplary user device 150. In various embodiments, elements such as the health system servers 110 and user devices 150, or portions thereof, may or may not themselves be part of the inventive system. For example, in some embodiments, the modeling server 130 only, or operation thereof, or elements of the modeling server 130, or elements of operation thereof, may constitute an entire inventive system, method, apparatus, architecture, data structure, computer readable media, etc.

It is to be understood that intermediary entities may be present in addition to those depicted, or multiple separate sub-entities of particular entities, and data may be received and sent from such non-depicted intermediaries or sub-entities to, from or within depicted entities. It is further to be understood that, while a single health system server 110, data server 120, modeling server 130, business intelligence (BI) server 140, and user device 150 are depicted, each engine can be implemented by or using one or more networks, computers, servers, clients, applications, operating systems, software, hardware, etc., as well as various communications therebetween.

Health system servers 110 receiving and storing EMR data may be located at or associated with various sites, such as hospitals, medical facilities, doctor's offices, etc. EMR data may be entered, logged, recorded or input at such sites. For example, upon admission of a patient into a hospital, EMR data relating to the patient, e.g. patent's name, patient's demographics, billing information, insurance information, health-related complaint, lab tests ordered for diagnosis, collected vitals or other data, prescriptions, diagnoses, surgery history, and many other types of data, may be entered, recorded or logged, or collected and entered, recorded or logged, into the hospital's computerized EMR system. In addition, other types of EMR data may be entered.

EMR data entered or logged into the health system servers 110 may immediately, such as in real time or near real time, be sent as a stream of data items directly, indirectly or via intermediary entities. Depending on specific circumstances, real time or near real time can be, for example, within seconds or a fraction of a second. In various embodiments, the EMR data sent from the health system servers 110 may be in various forms and formats, such as not yet formatted into HL7 messages, partially formatted into HL7 messages, or fully formatted into HL7 messages. EMR and other data present in health system servers 110 may be transmitted to data servers 120 and/or modeling servers 130 where one or more machine learning models may operate on the EMR data to derive risk estimates for ACS or other medical conditions, diagnoses, or diseases for one or more patients. BI server 140 compiles incoming query requests from users (e.g. ED physicians and other clinicians) via a user interface client running on user device 150 and translates the data to SQL or other readable query format and sends the request to back-end databases at data servers 120 and modeling servers 130. BI server 140 will also receive the query results and prepare the data results for display on the user interface running on user device 150.

Figure 2:
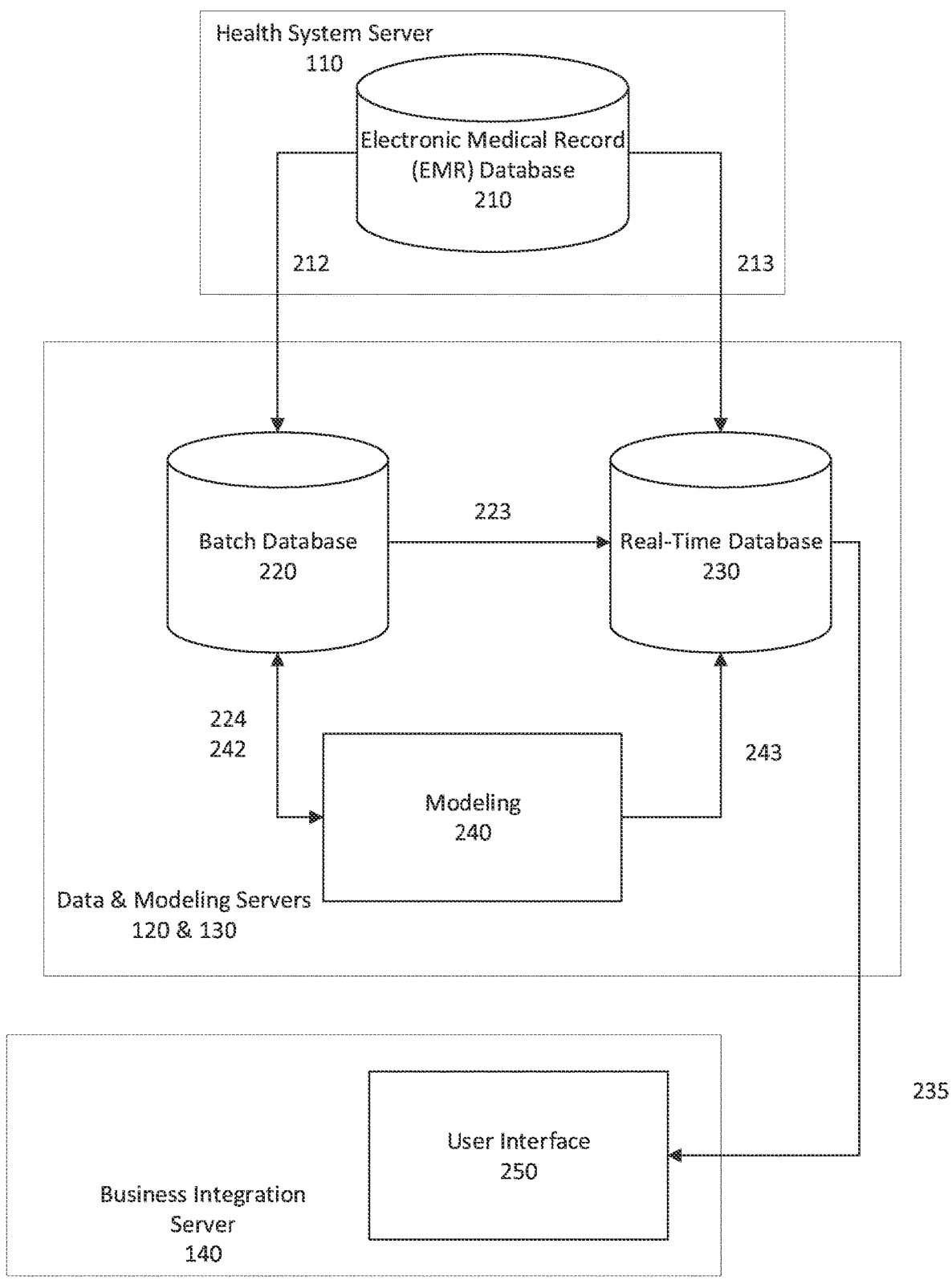
FIG. 2 illustrates a block diagram of the data flow and architecture of a system according to some embodiments of the invention.

FIG. 2 is a block diagram of the data flow and architecture of a system 200 according to some embodiments of the invention. Health system server 110 includes one or more EMR databases 210. Health system server 110 is connected to one or more data servers 120 and modeling servers 130. In various embodiments of the invention, one or more data servers 120 and modeling servers 130 comprise a batch database 220 and real-time database 230. Batch database 220 may be operably connected to health system server 110 and may receive batch data at pre-specified time intervals from EMR database 210 via network connection 212. In various embodiment of the invention, real-time database 230 may also be operably connected to health system 110 and may receive data in real-time or near real-time upon user request via network connection 213. Batch database 220 may also be operably connected to modeling engine 240 via network data connections 224 and 242, and to real-time database 230 via network data connection 223. Real-time database 230 is also connected to modeling engine 240 via network data connection 243. Real-time database 230 is also operably connected to business integration server 140 running user interface server program 250 via network data connection 235.

Figure 3:
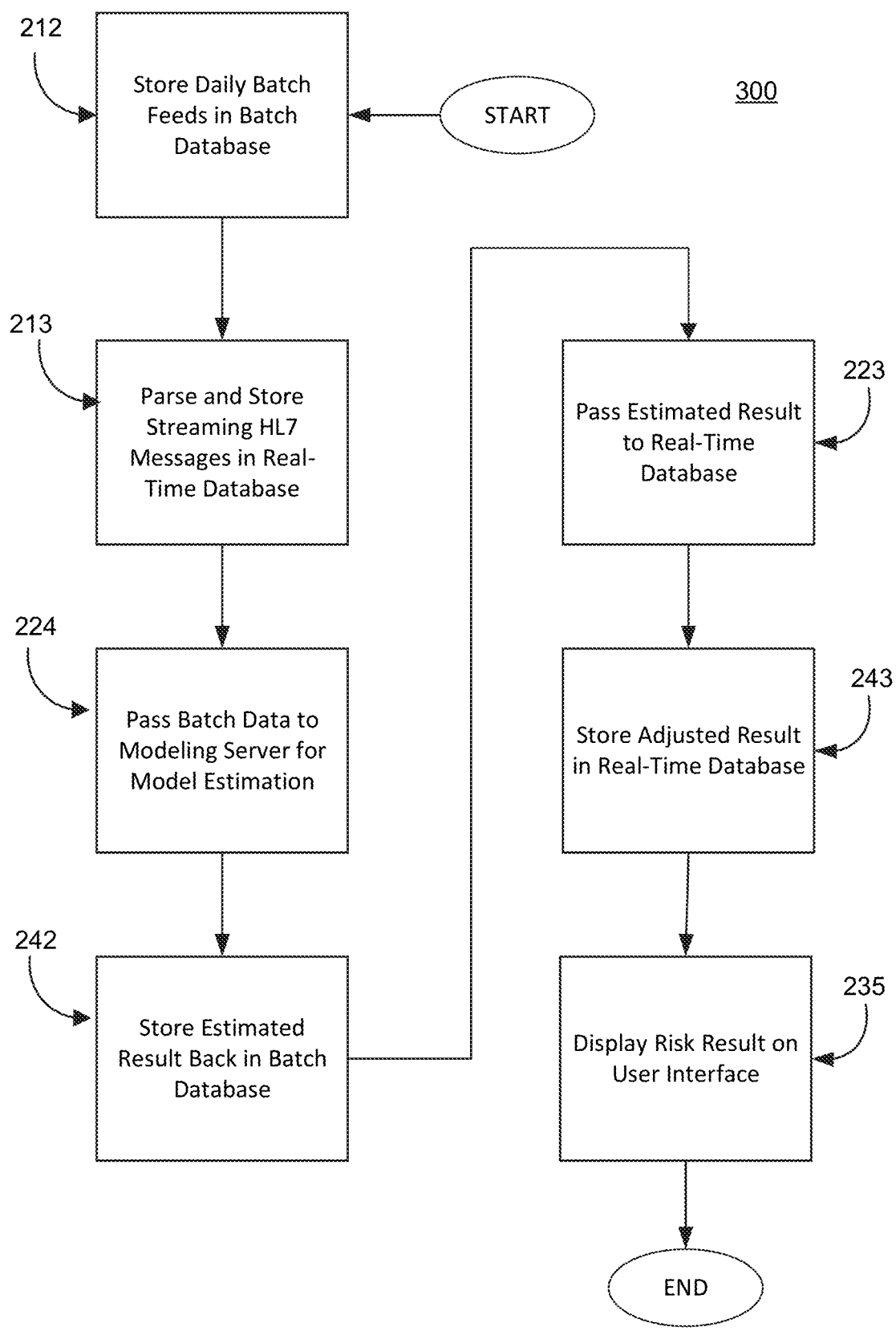
FIG. 3 illustrates a flow diagram of a method according to some embodiments of the invention.

FIG. 3 illustrates a flow diagram of a method 300 according to some embodiments of the invention and describes the data flows that were shown in FIG. 2 as network connections. In step 212, daily batch data feeds for patient records are retrieved from EMR database 210 and stored in the batch database 220. In step 213, streaming HL7 messages are stored in real-time database 230. In step 224, the daily batch data feeds from batch database 220 are passed to modeling server 240 for modeling estimation. In step 242, the estimated result is stored back in batch database 220. In step 223, the estimated result is passed from batch database 220 to real-time database 230. In step 243, the adjusted result is stored in real time database 230, and in step 235, the risk estimate result is displayed on user interface 250.

Figure 4:
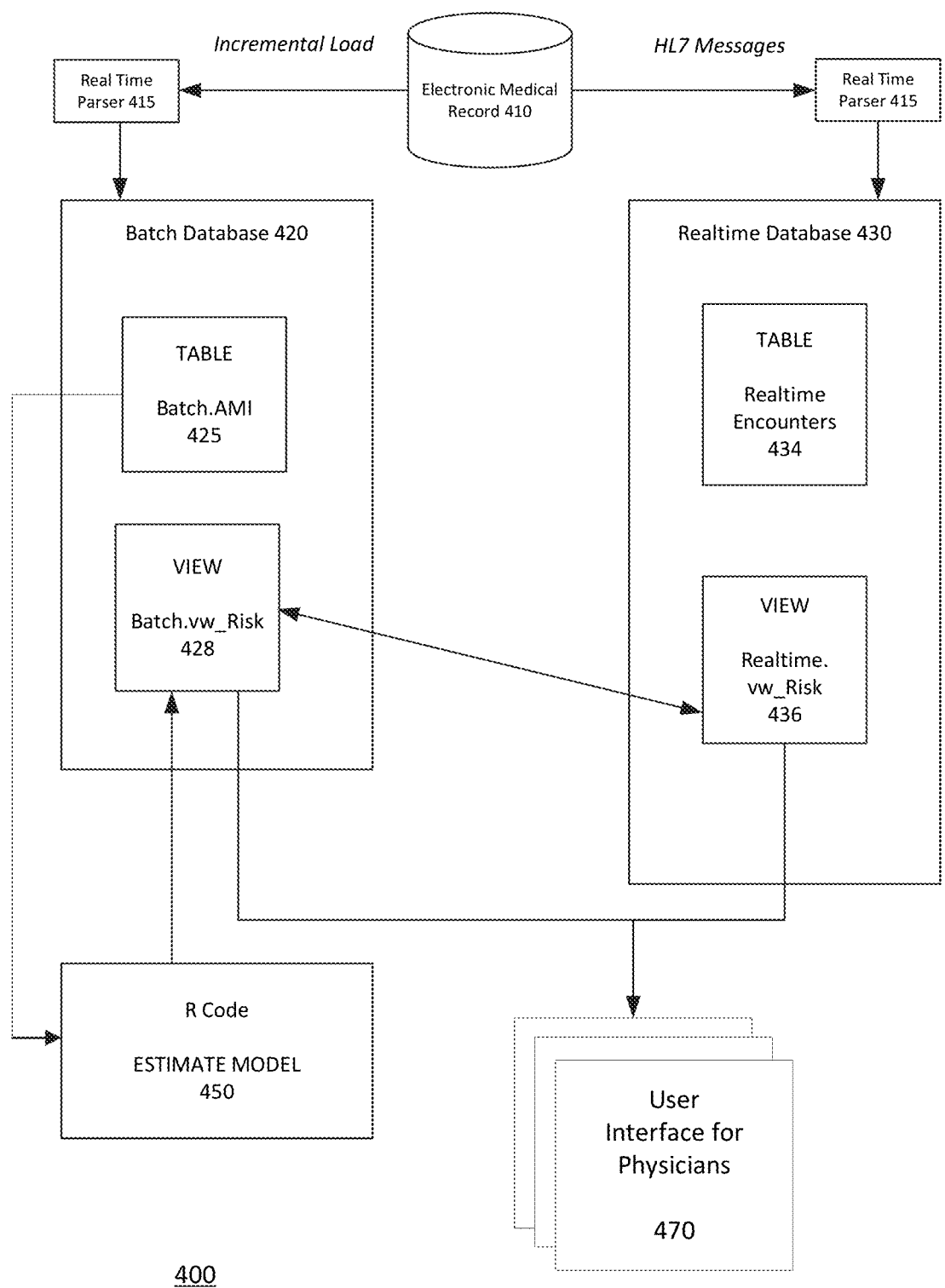
FIG. 4 illustrates an exemplary architecture for a system for providing real-time risk estimates for acute myocardial infarctions according to some embodiments of the invention.

Embodiments of the present invention provide a 'cached predictions' architecture by utilizing actual patient EMR data in machine learning technologies to provide real-time risk estimates for acute myocardial infarctions for patients presenting in the hospital ED. However, all patient data used for illustrative purposes in this patent specification is obscured and provided for illustrative purposes only and is not based in any way on actual patient EMR data. In order to protect the privacy of patients' highly sensitive data from the electronic medical record, embodiments of the present invention utilize guidelines from the Health Insurance Portability and Accountability Act of 1996 (HIPAA) Privacy Rule to de-identify all protected health information (PHI) utilized in embodiments of the present invention. Embodiments of the present invention utilize the Safe Harbor guidance available from the U.S. Department of Health and Human Services (hhs.gov/hipaa/for-professionals/privacy/special-topics/de-identification/index.html#safeharborguidance) to remove the at least the following classes of information listed under § 164.514(b):

FIG. 4 shows an exemplary architecture for a simplified system 400 for providing, in real-time or near-real-time, risk estimates for acute coronary syndrome. In some embodiments of the present invention, electronic medical records database 410 comprises the data store for the full electronic medical records (EMRs) for all patients served or treated by the hospital or health system that administers, maintains and uses EMR database 410. EMR database 410 may be operably connected to batch database 420 via real time parser 415 for extracting specified data via incremental data loads at specified time intervals. EMR database 410 may also be operably connected to real-time database 430 via real time parser 415 for extracting specified data from real-time or near real-time data transmissions of relevant current EMR data via HL7 messaging. Other patent applications describe exemplary embodiments of a real-time parser for use with EMR database 410 in detail, including, but not limited to, co-pending U.S. patent application Ser. No. 16/297,456, filed on Mar. 8, 2019, which is herein incorporated by reference in its entirety.

In some embodiments of the present invention, batch database 420 includes Batch.AMI 425 which shows as a primary database that represents the electronic medical record for patients having AMI data. The data included in the database table of Batch.AMI 425 is updated in batch each day. One relevant analogy here is taking a single snapshot of the electronic medical record each day. All necessary relevant information for the simple machine learning model implemented in system 400 is stored into a single table 425 (Batch.AMI). This table forms the basis for R code estimate model 450 that is used to estimate an encounter's probability of acute coronary syndrome. Although thousands of features may be contemplated in the estimate model used in other embodiments of the present invention, for the purposes of illustration for this discussion of one embodiment of the invention in conjunction with FIG. 4 focuses on three particular features: (1) age, (2) gender, and (3) the number of years since a patient's last episode of acute coronary syndrome.

R code. In one embodiment of the present invention, the R programming language and free software environment for statistical computing (r-project.org) is used as a scripting language to train and evaluate a machine learning model, as shown in R code estimate model 450. In this simplified example, a generalized linear model from the core R libraries is used. Any model generally can be described as a series of learned weights, or coefficients. The coefficients in this simplified example are deployed by translating them from R into SQL. This is useful because the deployment used in some embodiments of the present invention happens within the database only and without any dependencies on R.

In some embodiments of the present invention implementing the Batch.vw_Risk view component 428, the risk estimate is precalculated for each patient in the electronic medical record database 410 by 'simulating' that they will walk into the emergency department that day.

Realtime.Encounters database table 434 is implemented in embodiments of the present invention to address the temporal problem that results when a patient walks into the emergency department at any time, but they won't appear in the batch database until the next incremental load of data (particularly if this is their first visit to this hospital/health system/EMR administrator). Thus, if the batch database is run in the early morning, for patients that arrive in the emergency department for the first time in the afternoon, those patients' first appearance in the batch database wouldn't be until the next morning. However, the cardiac risk prediction tool of the present invention should be available to the clinician for evaluating all patients, and therefore should be available regardless of who the patient is for the first patient exam in the emergency department. To get around this temporal problem, some embodiments of the present invention comprise an additional real-time encounters database 434 constructed from streams of real-time HL7 messages. This additional real-time encounters database 434 can be accessed to serve a prediction to a physician the moment a patient—any patient—walks into the emergency department.

Realtime.vw_Risk component 436 provides the backend view needed to serve a prediction in a graphical user interface 470 in real-time, and in the simplified exemplary embodiment here may be implemented simply a join between the model predictions (Batch.vw_Risk) and the real-time encounters (Realtime.encounters real-time database) based on the person.

Data

Privacy protected data utilized in embodiments of the present invention can represent multiple observations of a person across different times, and therefore may be referred to as, e.g. 'panel' or 'longitudinal' data. Data rows are not independent from one another, as multiple encounters of a single person will be related. Embodiments of the present invention therefore utilize a patient's medical history to predict the likelihood of acute myocardial infarctions in the future.

Figure 5:
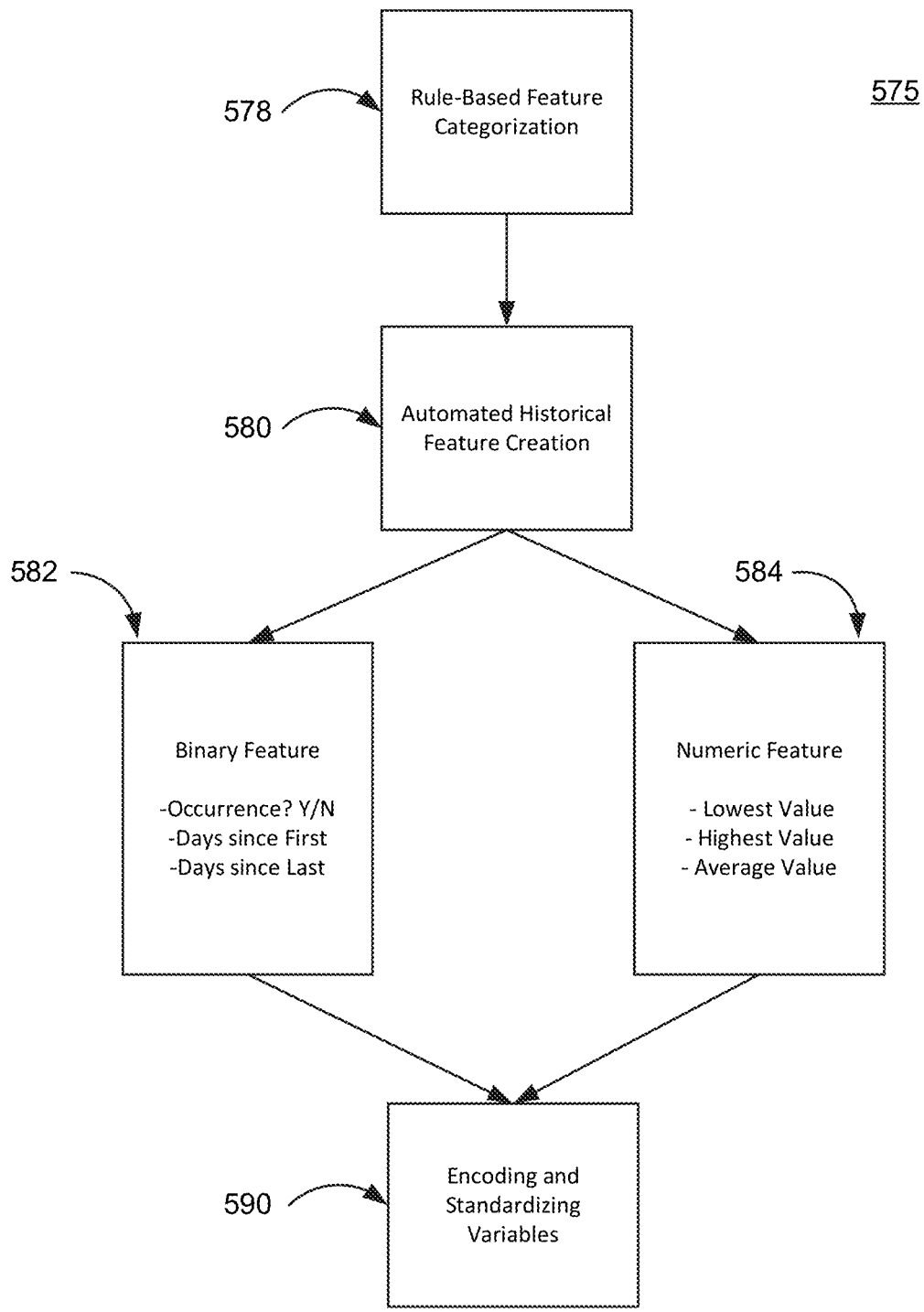
FIG. 5 illustrates an exemplary model preprocessing flow according to some embodiments of the invention.

FIG. 5 illustrates an exemplary model preprocessing flow 575 for historical EMR data according to some embodiments of the invention. This preprocessing flow may be run on the EMR data and stored in the batch database. Step 578 indicates a rule-based feature categorization that will determine whether a particular feature extracted from the EMR data is a binary feature (e.g., occurrence of AMI on first encounter, male/female gender classification), or a numeric feature (e.g., age). Step 580 will then automatically create a historical feature for the model using the EMR data, which could be a binary feature 582 which may include a yes/no or present/not present binary value, and if the value is "present," for example, the number of days since the last occurrence. Alternatively, the historical feature could be a numeric value 584 (e.g. an LDL or HDL cholesterol level, or a troponin level), which could store the current value, as well as a historical maximum, minimum and average value. Once the feature has been created, the feature is then encoded in a standard format 590, e.g., depending on whether it is a binary or numeric feature, or is related to diagnosis, procedures, medications, or diagnostic tests, for example, and then stored in the real-time or batch database.

In the simplified example below, we show a patient with 4 encounters. They experienced an acute myocardial infarction (AMI=1) on their first encounter but never again on their 2nd, 3rd, or 4th encounter in the hospital.

Below is a sample code snippet to run the batch search in the Electronic Medical Record database for the patient in this simplified example:

Select top 10
  Encounter
  ,Person
  ,YearBirth
  ,YearAdmit - YearBirth as Age ,YearAdmit - YearAMI as YearsSinceLastAMI
,case when Sex = 'Male' then 1 else 0 end as Male
,AMI
from Batch.AMI where Person = 123456
  Features
  In the simple linear model described below for some embodiments of the present invention, the probability of a patient experiencing an AMI on the present encounter (e.g. on the emergency department stay) or within 30 days of discharge is estimated. In this simplified example embodiment, the cardiac risk estimate of a patient is based on three fundamental factors:
  Age—In one sample patient population against which embodiments of the present invention have been tested, the incidence of AMI increases with age.
  Gender—In one sample patient population against which embodiments of the present invention have been tested, men have nearly double the incidence of AMI relative to women.
  Patient history of AMI—In one sample patient population against which embodiments of the present invention have been tested, those who have had a heart attack before are found to be more likely to have one in the future. In this simplified example embodiment discussed here, a more resolved feature is included that keeps track of the number of days between the present encounter and the patient's last heart attack.
  If a patient has never been seen before, they will have a missing history that is not retrievable from the EMR database. To get around this problem, a feature related to patient history of AMI has been imputed with the max. The logic here is that the relationship is expected to be weaker the longer the time has been, and so we chunk all the missing information into the right-hand side of the distribution.

```
# impute with max
dt[is,na(YearsSinceLastAMI),YearsSinceLastAMI := max(dt$YearsSinceLastAMI, na.rm=T)+1]
```

Simplified Model

A logistic regression model is used in this simplified example embodiment to assign a probability of an AMI to each encounter. In other embodiments of the present invention, a much more flexible approximation of risk may be applied to describe this probability as a nonlinear function of dozens, hundreds, or even thousands of features.

```
# estimate the model
fit <- glm(
    AMI ~ Male + Age + Male*Age + YearsSinceLastAMI ,
    data = dt,
    family = "binomial"
)
# show coefficients
summary(fit)

Call:
glm(formula = AMI ~ Male + Age + Male * Age + YearsSinceLastAMI,
family = "binomial", data = dt)

Deviance Residuals:
Min       1Q     Median       3Q       Max
-0.7673  -0.1361   -0.0831   -0.0540    3.9680

Coefficients:
Estimate   Std. Error   z value    Pr(>|z|)
(Intercept)          -6.861204   0.128039   -53.587   < 0.0000000000000002 ***
Male                  1.739251   0.136034    12.785   < 0.0000000000000002 ***
Age                   0.058366   0.001541    37.877   < 0.0000000000000002 ***
YearsSinceLastAMI    -0.353283   0.009592   -36.832   < 0.0000000000000002 ***
Male:Age             -0.013369   0.001896    -7.052     0.00000000000176 ***
---
Signif. codes:  0 '*' 0.001 '' 0.01 '*' 0.05 '.' 0.1 ' ' 1

(Dispersion parameter for binomial family taken to be 1)

Null deviance: 53373 on 615755 degrees of freedom
Residual deviance: 47372 on 615751 degrees of freedom
AIC: 47382

Number of Fisher Scoring iterations: 9
```

Production

The model used in this simplified example embodiment may be deployed to our database in Batch.vw_Risk by simply by translating the logistic regression coefficients to SQL.

```
tidypredict::tidypredict_sql(
    fit,                              # send in the logistic model
    con = dbplyr::simulate_mssql( )   # simulate a MS SQL Server
)                                     # connection
<SQL> 1.0 - 1.0 / (1.0 + EXP(-6.86120362193572 + ('Male') *
(1.73925063850959) + ('Age') * (0.0583664398975704) +
('YearsSinceLastAMI') * (-0.353283335905056) + (('Age') *
('Male')) * (-0.0133687071217581)))
```

The Batch.vw_Risk table may be created by abstracting the original table built from this model in the database, Batch.AMI. This table represents actual events, and the goal is to translate it into a format that can be useful for production. In other words, Batch.AMI represents 'what actually happened'.

-- our original table, 1 row per encounter
select
    Encounter
    ,Person
    ,YearAdmit
    ,YearAdmit - YearBirth as Age

```
,YearAdmit - YearAMI as YearsSinceLastAMI
,case when Sex = 'Male' then 1 else 0 end as Male
,AMI
from Batch.AMI where Person = 123456
```

Batch.vw_Risk represents 'what would happen if this patient walked into the emergency department today'

```
-- our production table, 1 row per person
select distinct
  Person
  ,datepart(year,getdate( )) - YearBirth as Age
  -- imputed feature handled with case Logic
  ,case
    when max(YearAMI) over (partition by person) is null
      then 6 -- impute with max
    else datepart(year,getdate( )) - max(YearAMI) over (par-
      tition by person) -- otherwise real value
    end as YearsSinceLastAMI
  -- sql handles binary [0-1] indicator better than factor level
  ,case when Sex = 'Male' then 1 else 0 end as Male
from Batch.AMI
where Person = 123456
```

The coefficients from the logistic regression model described above may be applied directly on top of this new representation of Batch.AMI. This code below shows how that can be done for a single person, but the same logic is applied without the 'where' clause in Batch.vw_Risk.

predictions may be precalculated and cached in advance of their need. In essence, this exemplary deployment is a lookup table, and this allows predictions in real-time to be served.

Machine Learning Model Based on Historical Data

Embodiments of the present invention implement a machine learning model that is useful for clinicians. A machine learning model is constructed by applying an algorithm to a set of data (model=data+algorithm). Algorithms utilize data to 'learn' a set of coefficients. This machine learning model prepares useful data to feed into an algorithm. One machine learning model used in some embodiments of the present invention is called a Gradient Boosting Machine. A Gradient Boosting Machine is a machine learning technique for regression and classification problems. The guiding heuristic is that good predictive results can be obtained through increasingly refined approximations. In an embodiment of the present invention, a Gradient Boosting Machine sequentially builds regression decision trees on the features of the dataset in parallel.

One embodiment of the present invention implements the Gradient Boosting Machine available to implement in H2O 3 (docs.h2o.ai/h2o/latest-stable/h2o-docs/welcome.html), an open source, in memory, distributed, fast, and scalable machine learning and predictive analytics platform that allows users to build various machine learning models on big data and provides easy systems to put these models into

```
-- make a cte to do the feature engineering
with base as
(
select distinct
  Person
  ,datepart(year,getdate( )) - YearBirth as Age
  -- imputed feature handled with case Logic
  ,case
      when max(YearAMI) over (partition by person) is null then 6
  -- impute with max
      else datepart(year,getdate( )) - max(YearAMI) over (partition by person
) -- otherwise real value
    end as YearsSinceLastAMI
  -- sql handles binary [0-1] indicator better than factor level
  ,case when Sex = 'Male' then 1 else 0 end as Male
from Batch.AMI
where Person = 123456
)
-- apply the coefficients from tidypredict to the features
select
  -- 1 row per person
  Person
  -- Logistic regression, so 1 - 1/(1+exp(X*Beta))
  ,1.0 - 1.0 / (1.0 + EXP(
    -6.77184061085251                                  -- intercept
    + ("Male") * (1.61408800675687)                    -- term for male
    + ("Age") * (0.0558370565066422)                   -- term for age
    + ("YearsSinceLastAMI") * (-0.342169455821517)     -- term for patient history
    + (("Age") * ("Male")) * (-0.0110550139836667)     --interaction term
  )) as Probability
from base
```

The last step for the deployment is simply to join the view, Batch.vw_Risk, to a real-time database Realtime.Encounters based on the person. This will provide a probability of AMI as soon as there is a matching person from the stream of HL7 messages.

The cardiac risk prediction system described in this and other embodiments of the present invention solve a common problem in machine learning. The cardiac risk prediction machine learning model is based on features in a batch database, but users (i.e., clinicians) need predictions from this model in real-time. To get around this discrepancy, production. However, any of a variety of different machine learning models, both available to implement in H2O 3 and other platforms, both open source and commercial, may be used without departing from the spirit and scope of the present invention.

One difficult aspect of building predictive models for clinicians is feature engineering. This problem is magnified when there is a need across different vendors of electronic medical records. There has been some recent progress in building universal features directly from the electronic medical record with deep learning (Rajkomar et al. 2018).

As computational resources are limited, embodiments of the present invention implement a set of routines based on a domain knowledge of healthcare that can help make clinical predictions accessible to a wider audience.

Rajkomar A, Oren E, Chen K, Dai A M, Hajaj N, Hardt M, Liu P J, Liu X, Marcus J, Sun M, Sundberg P. Scalable and accurate deep learning with electronic health records. NPJ Digital Medicine. 2018 May 8; 1(1):18

In embodiments of the present invention, a set of feature engineering routines is constructed in a relational database. In one embodiment of the present invention, these routines may be translated from SQL into R programming language.

Definitions Used

Person—healthcare is a people business and therefore it is critical to keep track of patient (people) data.

Encounter—e.g. a 'row' in the data base is meant to represent an encounter, or episode of care. For example, if a person walks into the emergency department→is admitted as an inpatient to the hospital→transferred to surgery→recovers in the inpatient ward→and then is discharged to home, this is considered a single episode of care.

Simple Example Based on Historical Data

Clinical events are generally stored in normalized (e.g. long) tables in a data warehouse. In this case, each encounter–reason combination will be represented as a row. The below example relational database table utilizes made-up data:

| Person | Encounter | Date | Reason |
|---|---|---|---|
| John | Encounter 1 John | 2017 Jan. 1 | Elective Surgery |
| John | Encounter 2 John | 2017 Jun. 5 | Deep Vein Thrombosis |
| John | Encounter 3 John | 2018 Feb. 3 | Elective Surgery |
| Susy | Encounter 1 Susy | 2018 May 3 | Heart Attack |
| Susy | Encounter 2 Susy | 2018 May 10 | Elective Surgery |

This compact format is useful to reduce storage space in a data warehouse but is not useful for a machine learning model. Models generally expect a single set of rows (observations) and columns (features). In the case below, a dummy column is made for each reason for visit and is coded at 1 (reason is present) or 0 (reason is absent). In machine learning speak this transformation is simply a 'one-hot encoding' where 1 factor level becomes 1 column:

| Person | Encounter | Date | Deep Vein Thrombosis | Elective Surgery | Heart Attack |
|---|---|---|---|---|---|
| John | Encounter 1 John | 2017 Jan. 1 | 0 | 1 | 0 |
| John | Encounter 2 John | 2017 Jun. 5 | 1 | 0 | 0 |
| John | Encounter 3 John | 2018 Feb. 3 | 0 | 1 | 0 |
| Susy | Encounter 1 Susy | 2018 May 3 | 0 | 0 | 1 |
| Susy | Encounter 2 Susy | 2018 May 10 | 0 | 1 | 0 |

The clinical machine learning model provides a cross-section of patients across time. In other domains these are often referred to as 'longitudinal' or 'panel' data. In this clinical machine learning model, there is relevant information in a patient's medical history to inform the risk estimate of events in the present encounter. In the case of John, a history of surgery could be used as a predictor for future episode of deep vein thrombosis. This differs from one-hot encoding in that a 1 represents a positive patient history of a factor level as opposed to a positive factor level within that encounter:

| Person | Encounter | Date | Hx Of Deep Vein Thrombosis | Hx Of Elective Surgery | Hx Of Heart Attack |
|---|---|---|---|---|---|
| John | Encounter 1 John | 2017 Jan. 1 | 0 | 0 | 0 |
| John | Encounter 2 John | 2017 Jun. 5 | 0 | 1 | 0 |
| John | Encounter 3 John | 2018 Feb. 3 | 1 | 1 | 0 |
| Susy | Encounter 1 Susy | 2018 May 3 | 0 | 0 | 0 |
| Susy | Encounter 2 Susy | 2018 May 10 | 0 | 0 | 1 |

One reason "1 hot" encoding is avoided in clinical models used in embodiments of the present invention is that features derived from the present encounter are generally not available during production. For example, most billing records that are not created until weeks after a patient is discharged. A model constructed on billing records for the present encounter would not necessarily be able to make predictions for patients currently in the hospital, particularly those without prior encounters at this health care system.

Another reason "1 hot" encoding is avoided in clinical models is that it can be difficult to understand causal relationships in healthcare without a medical degree. For example, if a clinical model uses the administration of acetaminophen (aka, "Tylenol" brand pain reliever) as a 'predictor' for headaches, this is incorrect as it has causation backwards. By relying on a patient's medical history, all features are in the past. In general, the past can safely be used to predict future medical events without having to worry about getting the causation backwards.

Example with Fictional Data

This example shows how data ingestion routines implemented in some embodiments of the present invention can build a predictive model for acute myocardial infarctions, or heart attacks. This builds on the simple model discussed at the beginning of the Description section of this specification, based on a patient's age, gender, and history of recent heart attacks. In particular, this exemplary machine learning model includes additional features derived from a patient's medical history:

DRGs, or diagnosis related groups, are useful classifications of medical encounters. These several hundred DRG codes are rolled up further into Major Diagnosis Categories, or MDC.

Models require denormalized (or wide) tales to do anything useful. Routines implemented in some embodiments of the present invention standardize these transformations into a set of columns. This set of columns is used in some embodiments of the present invention to quickly build out predictive models for a variety of unrelated medical use cases.

This denormalize function takes a data.frame (x) as well as a mapping function. Let's start with the data.

The data should be in the following (normalized) format with these column names:

encounter—a unique identifier across all episodes of care (or people going to seek medical treatment).

person—a unique identifier across all people who have visited your health system.

ds—a valid datestamp for that row. This datestamp is used to track people and order over time.

category—what happened? this factor level will get turned into a column.

These data elements, and others, should be relatively simple to retrieve directly from a data warehouse. In the code example below, 8 total records (not shown) may be retrieved for a selected patient showing 8 different encounter dates, showing different major diagnosis categories, or MDCs:

select
   Encounter as encounter - fake
   ,Person as person - fake
   ,Admit as ds - these dates are fake, but the distance between them is real.
   ,left(lower(CategoryNM),40) as category - for printing, entire name is used from Batch.History
where CategoryDSC = 'binary' - focus on events for now
and Person = 123456
order by Person, Admit

| encounter | person | ds | Category |
|---|---|---|---|
| 1111110 | 123456 | 1989 Feb. 1 | mdc diseases & disorders of the respirat |
| 1111111 | 123456 | 1991 Jul. 3 | mdc diseases & disorders of the hepatobi |
| 1111112 | 123456 | 1995 Apr. 7 | mdc diseases & disorders of the circulat |
| 1111113 | 123456 | 1996 Jun. 29 | mdc diseases & disorders of the circulat |
| 1111114 | 123456 | 1996 Sep. 8 | mdc infectious & parasitic diseases, sys |
| 1111115 | 123456 | 1997 Dec. 22 | mdc diseases & disorders of the hepatobi |
| 1111116 | 123456 | 1997 Nov. 27 | mdc diseases & disorders of the circulat |
| 1111117 | 123456 | 1998 Mar. 30 | mdc diseases & disorders of the circulat |

Before the machine learning data model can begin widening the data from factor levels to columns, a mapping function below may be used to create nicely formatted column names. Below is an exemplary mapping function used in some embodiments of the present invention where any string, for example, 'Heart Attacks Within 6' (months) may be converted to camel case, i.e., 'HeartAttacksWithin6' without spaces, underscores, or special characters:

```
mapping <- function(x){
  # from the documentation of toupper( ) in base R
  capwords <- function(s) {
    cap <- function(s)
      paste(toupper(substring(s, 1, 1)),{s <- substrings(s, 2); }, sep = " ",
collapse = " " )
    sapply(strsplit(s, spilt = " "), cap, USE.NAMES = !is.null(names(s)))
  }
  x %>%
    tolower( ) %>% #
    gsub("[[:punct:]]", "", .) %>% # remove special
    gsub(" ", " ", .) %>%         # remove double white
    capwords( ) %>%
    gsub(" ", "", .)              # no spaces
}
```

The denormalize function (see appendix) is used to get a useful representation of these data for modeling. The denormalize function may pull data directly from a sample database while adhering to the 4 naming conventions (encounter, person, ds, category).

data <- denormalize(
   # your data with the expected names
   x = DBI::dbGetQuery(
   gemini,
   "
     select
       Encounter as encounter -- fake
       ,Person as person -- fake
       ,Admit as ds- these dates are fake, but the distance between them is real
       ,CategoryNM as category
     from Batch.History
     where CategoryOSC = 'binary' -- focus on events for now
     and Person = 123456
     order by Person
   "
   )
   # a mapping function to clean up a column name
   mapping = mapping
)

This function takes the 2 major diagnostic categories that were present in the historical data and made 6 columns (2*3). The first column (HxBinaryMdcDiseasesDisordersOfTheCirculatorySystem) is a binary indicator if that level has occurred before.

The second column (HxLastMdcDiseasesDisordersOfTheCirculatorySystem) calculates the number of days between the PRESENT encounter and the LAST time this category was recorded. This is a useful feature if a recent history is indicative of future problems (like heart attacks predicting heart attacks).

The third column (HxFirstMdcDiseasesDisordersOfTheCirculatorySystem) calculates the number of days between the PRESENT encounter and the FIRST time this category was recorded. This is useful is a long history is useful of future problems (like diabetes predicting end stage renal disease).

Note, if an event has only happened once before in a patient's history, the FIRST and LAST time it has happened will be the same. As more information is gathered from a patient over subsequent visits these two fields diverge.

Applying the Model

The denormalize function is applied over the entire sample de-identified dataset. In the previous example the denormalization was only done for 1 patient.

```
dt <- denormalize(
  # your data with the expected names
  x = DBI::dbGetQuery(
    gemini,
    "
    select
      Encounter as encounter -- fake
      ,Person as person -- fake
      ,Admit as ds -- these dates are fake, but the distance
        between the is real
      ,CategoryNM as category
    from Batch.History
    where CategoryDSC = 'binary' -- focus on events for now
    order by Person
    "
  )
  # a mapping function to clean up a column name
  mapping = mapping
)
```

Now that there is a set of data for modeling, the next step would be to join in the feature (Years Since Last AMI), which are stored in the Batch.AMI table.

```
# retrieve
batch <- DBI::dbGetQuery(gemini,
  "
  select
    Encounter as encounter
    ,YearAdmit - YearBirth as Age
    ,YearAdmit - YearAMI as YearsSinceLastAMI
    ,Sex
    ,case with Sex = 'Male' then 1 else 0 end as Male
    AMI
  from Bath.AMI
  "
)
setDT(batch)
# merge
data.table::setkey(batch,"encounter")
data.table::setkey(dt,"encounter")
dt <- merge(batch,dt)
#*impute with max
dt[is.na(YearsSinceLastAMI),YearsSinceLastAMI max(dt-
  $YearsSinceLastAMI,na.rm=T)+1]
```

If the data is split into different regions, this will validate any signal we estimate on the training region is generalizable to new patients, and not just fitting to noise. In this exemplary code below, the data is split into train/validation regions which will lump all the encounters of a single person into either train/validation regions (but not both). A 50:50 split between train/validation regions is the initial setting for now.

```
# return a List of row assignments
splits <- vtreat::buildEvalSets(
  nRows=nrow(dt),
  dframe = dt,
  y = dt$AMI,
  splitFunction   =   vtreat::makekWayCrossValidation-
GroupedByColumn("person"),
  nSplits = 2
)
# subset into disjoint sets
dt_train <- dt[splits[[1]]$app,]
dt_valid <- dt[splits[[2]]$app,]
# check to make sure there is not overlap
sum(dt_train$Person Uri % dt_valid$Person)
[1] 0
sum(dt_train$Encounter %in% dt_valid$Encounter)
[1] 0
```

The previous model demonstrated in the first example in the Description section of this patent specification was based on only four features. A patient's age, gender, and the number of years since their last acute myocardial infarction.

```
old <- glm(
  AMI ~ Male + Age + Male*Age + YearsSinceLastAMI ,
  data = dt_train,
  family = "binomial"
)
# show coefficients
summary(old)

Call:
glm(formula = AMI ~ Male + Age +Male * Age + YearsSinceLastAMI,
family = "binomial", data = dt_train)

Deviance Residuals:
Min         1Q     Median         3Q        Max
-0.8524    -0.3118    -0.2572    -0.1922     3.2346
Coefficients:
Estimate   Std. Error   z value       Pr>|z|)
(Intercept)       -4.290660   0.215222    -19.936 <   0.0000000000000002 ***
Male               1.329483   0.226705      5.864       0.00000000451    ***
Age                0.032738   0.002583     12.675 <   0.0000000000000002 ***
YearsSinceLastAMI -0.259557   0.016893    -15.364 <   0.0000000000000002 ***
Male:Age          -0.009008   0.003165     -2.846       0.00443          **
---
Signif. codes: 0 '*' 0.001 '' 0.01 '*' 0.05 '.' 0.1 ' ' 1

```

```
(Dispersion parameter for binomial family taken to be 1)

Null deviance: 15323  on 47537  degrees of freedom
Residual deviance: 14530  on 47533  degrees of freedom
AIC: 14540

Number of Fisher Scoring iterations: 7
```

In the example code below, a new model is constructed with only binary indicators of patient history from the routines. Note, this excludes the numeric columns of the number of days between the present and the FIRST/LAST time X happened.

```
# what columns to include
history      <-      names(dt_train)[grepl("HxBinary",
names(dt_train))]
history <- history[sapply(dt[,..history],function(x) sum(x)
>0)]
# build a model
new <- glm(
   paste0("AMI ~
Male + Age + Male*Age + YearsSinceLastAMI +",
   paste(history, collapse = "+")
   ),
   data = dt_train,
   family = "binomial"
)
```

A model's performance may be measured by its area under the receiver operator characteristic curve (AUROC) in some embodiments of the present invention. The AUROC is a metric that ranges from 0.5 (random guess) to 1 (perfect classifier). In rough terms it can be described as weighing the tradeoffs between true positives and false positives over all possible combinations.

The AUROC of the model with additional features performs better because more features would improve a model's ability to distinguish encounters with and without acute myocardial infarctions. DRG codes only are considered in this simplified example, and there would likely be a larger increase in performance if a patient's medical history of ICD codes, medications, procedures, etc. was included.

This machine learning model with new features used in some embodiments of the present invention generalizes well to new patients.

Healthcare data is complex with multiple observations of people across time. In the above described embodiments of the present invention, a set of transformations has been created to quickly construct robust clinical models based on a patient's medical history.

Adjusting the Historical Model Using Real-Time Data

Once the machine learning model is used to calculate the risk estimate of acute coronary syndrome or acute myocardial infarction (AMI) based on a patient's medical history, a next step for embodiments of the present invention would be to adjust the historical risk estimate in the model for acute coronary syndrome based on the derived features from the real-time database. The purpose of doing this is that is to build a complex nonlinear model based on a patient' medical history, then deploy a simple adjustment by translating a linear model to SQL. This means that one dependency in the real-time production system is SQL.

To deploy the adjustment, some embodiments of the present invention begin with the historical machine learning model constructed from the set of features from the batch database. An exemplary set of coefficients that may be used in some embodiments of the present invention is shown below.

```
coef(new)
(Intercept)
-3.880179441
Male
1.122951595
Age
0.030077764
YearsSinceLastAMI
-0.258690793
HxBinaryMdcAlcoholdrugUseAlcoholdrugInducedOrganicMentalDisor
-0.798850113
HxBinaryMdcBurns
-10.765345463
HxBinaryMdcDiseasesDisorderOfTheNervousSystem
-0.866597245
HxBinaryMdcDiseasesDisordersOfBloodBloodFormgOrgansImmunolog
-0.604336105
HxBinaryMdcDiseasesDisordersOfMusculoskeletalSystConnTissue
-0.448066443
HxBinaryMdcDiseasesDisordersOfSkinSubcutaneousTissueBreast
-0.603460772
HxBinaryMdcDiseasesDisordersOfTheCirculatorySystem
0.197638014
HxBinaryMdcDiseasesDisordersOfTheDigestiveSystem
-0.301368999
HxBinaryMdcDiseasesDisordersOfTheEarNoseMouthThroat
-0.342537505
HxBinaryMdcDiseasesDisordersOfTheEye
-12.579011783
HxBinaryMdcDiseasesDisordersOfTheFemalReproductiveSystem
-0.491955263
```

```
HxBinaryMdcDiseasesDisordersOfTheHepatobiliarySystemPancreas
-0.794774923
HxBinaryMdcDiseasesDisordersOfTheKidneyUrinaryTract
-0.374790467
HxBinaryMdcDiseasesDisordersOfTheMaleReproductiveSystem
-13.227612069
HxBinaryMdcDiseasesDisordersOfTheNervousSystem
-0.246697840
HxBinaryMdcDiseasesDisordersOfTheRespiratorySystem
-0.675926261
HxBinaryMdcEndocrineNutritionalMetabolicDiseasesDisorders
-0.492302099
HxBinaryMdcFactorsInfluencingHlthStatOthrContctsWithHlthSrvcs
-0.076641236
HxBinaryMdcHumanImmunodeficiencyVirusInfections
-12.467623734
HxBinaryMdcInfectiousParasiticDiseasesSystemicOrUnspecSites
-0.384227851
HxBinaryMdcInjuriesPoisoningsToxicEffectsOfDrugs
-0.560240744
HxBinaryMdcMentalDiseasesDisorders
-1.619705110
HxBinaryMdcMultipleSignificantTrauma
-1.061076417
HxBinaryMdcMyeloproliferativeDDPoorlyDifferentiatedNeoplasm
-0.455183894
HxBinaryMdcPregnancyChildbirthAndThePuerperium
-11.904926503
Male:Age
-0.006906733
```

Next, those coefficients may be adjusted by building a second model on top of them. This is just another way to accomplish dimensionality reduction and collapse N features into 1 vector.

```
# make a vector with the historical probabilities
dt_train[,HistoricalProbability := predict(new, dt_train, type="response")]
dt_valid[,HistoricalProbability := predict(new, dt_valid, type="response")]
```

Next, another model may be estimated on top of the first. Some simple reason for visit transformations may be used.

```
# which features to use
counts <- dt_train[,.N,by="ReasonForVistDSC"]
counts <- counts[N >100,]
counts <- counts[rev(order(N)),]
```

In some embodiments of the present invention, indicator columns can be added if a level is present. A few of the most prevalent reasons for visit are indicated below, e.g., mental health, behavioral health, chest pain, pneumonia, type of heart attack (ST-Elevation Myocardial Infarction (STEMI), or Non-ST-Elevation Myocardial Infarction (NSTEMI)).

```
dt_train[,ReasonLevMHU := ifelse(ReasonForVisitDSC=="MHU",1,0)] #mental health unit
dt_train[,ReasonLevBHU := ifelse(ReasonForVisitDSC=="BHu",1,0)] #behavioral health unit
dt_train[,ReasonLevCHESTPAIN:= ifelse(ReasonForVisitDSC %in% c("CHEST PAIN","ACUTE CHEST PAIN"),1,0)]
dt_train[,ReasonLevPNEUMONIA := ifelse(ReasonForVisitDSC=="PNEUMONIA",1,0)]
dt_train[,ReasonLevSTEMI := ifelse(ReasonForVisitDSC %in% c("STEMI","NSTEMI"),1,0)]
dt_valid[,ReasonLevMHU := ifelse(ReasonForVisitDSC=="MHU",1,0)] #mental health unit
dt_valid[,ReasonLevBHU := ifelse(ReasonForVisitDSC=="BHU",1,0)] #behavioral health unit
dt_valid[,ReasonLevCHESTPAIN := ifelse(ReasonForVisitDSC %in% c("CHEST PAIN","ACUTE CHEST PAIN"),1,0)]
dt_valid[,Reason LevPNEUMONIA := ifelse(ReasonForVisitDSC=="PNEUMONIA",1,0)]
dt_valid[,ReasonLevSTEMI := ifelse(ReasonForVisitDSC %in% c("STEMI","NSTEMI"),1,0)]
```

Real-time features are then added to the model.

```
#   build adjusted model
adjusted <- glm(
    AMI ~ HistoricalProbability + ReasonLevMHU + ReasonLevBHU + ReasonLevCHESTPAIN + ReasonLevPNEUMONIA + ReasonLevSTEMI,
    data = dt_train,
    family = "biomial"
)
summary(adjusted)

Call:
glm(formula = AMI ~ HistoricalProbability + ReasonLevMHU + ReasonLevBHU +
ReasonLevCHESTPAIN + ReasonLevPNEUMONIA + ReasonLevSTEMI,
family = "binomial", data = dt_train)
```

```
Deviance Residuals:

Min        1Q       Median      3Q       Max
-3.1695    -0.2531    -0.2236    -0.2019    3.9499

Coefficients:
Estimate Std.   Error    z value     Pr(>|z|)
(Intercept)          -4.03201     0.04027   -100.132   <  0.0000000000000002
HistoricalProbability 12.18883    0.50600    24.089   <  0.0000000000000002
ReasonLevMHU         -3.81114     0.99776    -3.820      0.000134
ReasonLevBHU         -3.46084     1.00030    -3.460      0.000541
ReasonLevCHESTPAIN    2.54357     0.08205    31.000   <  0.0000000000000002
ReasonLevPNEUMONIA   -1.27609     0.45152    -2.826      0.004710
ReasonLevSTEMI        5.85494     0.22490    26.034   <  0.0000000000000002

(Intercept)            ***
HistoricalProbability  ***
ReasonLevMHU           ***
ReasonLevBHU           ***
ReasonLevCHESTPAIN     ***
ReasonLevPNEUMONIA     **
ReasonLevSTEMI         ***
---
Signif. codes: 0 '*' 0.001 '' 0.01 '*' 0.05 '.' 0.1 ' ' 1

(Dispersion parameter for binomial family taken to be 1)

Null deviance: 15276 on 47260 degrees of freedom
Residual deviance: 12320 on 47254 degrees of freedom
AIC: 12334

Number of Fisher Scoring iterations: 9
```

As might be expected, when information is added about the present visit in embodiments of the present invention, it improves the AUROC curve.

Using the below exemplary code, the adjusted model may be deployed to a view based only on the coefficients. This is the entire purpose of this adjustment because in some embodiments of the present invention, it is desired to keep R outside of the real-time prediction architecture to allow for minimal dependencies. tidypredict::tidypredict_sql(

```
    adjusted,              # send in the logistic model
    con = dbplyr::simulate_mssql( ) # simulate o MS SQL server
connection
    )
<SQL> 1.0 - 1.0 / (1.0 + EXP(-4.03200891826347 +
('HistoricalProbability') * (12.1888250929767) +
('ReasonLevMHU') * (-3.81113755116061) +
('ReasonLevBHU') * (-3.46083757401234) + ('ReasonLevCHESTPAIN') *
(2.54357473900494) + ('ReasonLevPNEUMONIA') *
(-1.27608755638407) + ('ReasonLevSTEMI') * (5.85493601862095)))
```

Data is used in conjunction with algorithms to develop a machine learning model to stratify the risk estimation of acute coronary syndrome. Some embodiments of the present invention utilize a set of features from the electronic medical record with dozens, hundreds, or thousands of covariates.

Analogy

The electronic medical record is the source of facts, but the data may need to be cleaned up before it can be used. For example, if the EMR data may be thought of using an analogy to food, the EMRs themselves may be considered the farmers that grow produce. However, the produce harvested directly by the farmers may need to go through a chain of distribution, e.g. middlemen, before reaching the end user. Very few people go directly to farmers for their food.

Embodiments of the present invention utilize a middleman such as a healthcare analytics data operating system, e.g. Health Catalyst (healthcatalyst.com). A healthcare analytics data operating system is a middleman that helps extract information from the EMR and bring it into a useful representation in a data warehouse. Using the food analogy above, the healthcare analytics data operating system may be thought of as a middleman such as grocery store. Lots of people go to the grocery store to get food, but they still need to take it home and cook it.

Embodiments of the present invention construct higher order structures from the ingredients we find in the data warehouse. Just as many consumers are busy, embodiments of the present invention may be thought of like a restaurant. All a consumer needs to do is walk in and eat, no cooking necessary.

Some embodiments of the present invention map covariates in an EMR data system to EMR vendor agnostic categories. This is useful because it means we can scale across hospitals with different systems.

Covariates used in embodiments of the present invention may include, but are not limited to, the following exemplary classifications and categories:

[Dx] 279 clinical classifications software categories (e.g. septicemia, tuberculosis)

[Rx] 271 types of prescriptions (e.g. opiates, beta blockers)

[Sx] 476 distinct types of surgeries (e.g. paracentesis, orchiectomy)

[Svc] 74 types of medical services (e.g. obstetrics, surgery)

[Mdc] 25 major diagnostic categories (e.g. mental diseases, disorders of nervous system)

Taken together they represent a holistic view of a patient's history.

For each of these features we built out three columns.

[Hxb] Does this patient have a medical history of X?

[Hxl] How many days have passed since the last time X occurred?

[Hxf] How many days have passed since the first time X occurred?

If a feature is tagged with a 'Prev' prefix it means go back in that patient's history to the last visit. For example, 'PrevDischargeDays' means count the number of days between the current encounter and the previous discharge.

A number of preprocessing steps are performed prior to modeling in some embodiments of the present invention. An exemplary set of preprocessing steps used in some embodiments of the present invention is shown at FIG. 5 as described above.

CVDSC, a factor level from the database. No different from CVDisplayDSC.

_clean, just reminds us the column went through the processor

_catB, a bayesian impact code for that factor level.

_lev_x., a factor column that was turned into a dummy indicator

Other columns

DerivedAgeOverX—subtract X the patient's age

DerivedAgeBracketX—round the patient's age to X and build a factor level

ReadmitX—the encounter is a readmission within X window

Model

There are four separate classification models for each of the subcomponents of acute coronary syndrome that have been developed for use in some embodiments of the present invention. A classification model attempts to draw some conclusion from observed values. Given one or more inputs, a classification model will try to predict the value of one or more outcomes. Outcomes are labels that can be applied to a dataset. For example, when looking at EMR data for the likelihood of AMI, "admit" or "do not admit." There are two approaches to machine learning: supervised and unsupervised. In a supervised model, as here a training dataset is fed into the classification algorithm. That lets the model know what is, for example, a risk estimate of AMI sufficient to Admit. Then the test data sample is compared with that to determine if this patient should be admitted to the hospital. This type of learning falls under "Classification".

Acute Myocardial Infarctions (AMI)

| ## | | variable | percentage |
|---|---|---|---|
| ## | 1: | AgeInDays_clean | 0.172816016 |
| ## | 2: | HxbDxAcuteMyocardialInfarction_clean | 0.123481357 |
| ## | 3: | DerivedAgeOver50_clean | 0.072749208 |
| ## | 4: | DerivedAgeOver35_clean | 0.063574073 |
| ## | 5: | ReligionCVDSC_catB | 0.035637994 |
| ## | 6: | DerivedAgeBracket5_clean | 0.021964333 |
| ## | 7: | SexCVDisplayDSC_lev_x.Male | 0.016982959 |
| ## | 8: | ReligionCVDSC_lev_x.Unknown | 0.016182433 |
| ## | 9: | Zip_catB | 0.012502619 |
| ## | 10: | HxbDxCoronaryAtherosclerosisAndOtherHeartDisease_clean | 0.010341263 |
| ## | 11: | HxfDxCoronaryAtherosclerosisAndOtherHeartDisease_clean | 0.009916257 |
| ## | 12: | SexCVDisplayDSC_lev_x.Female | 0.009193818 |
| ## | 13: | PrevDischargeDispositionCVDSC_lev_x. | 0.009095155 |
| ## | 14: | SexCVDisplayDSC_catB | 0.008657482 |
| ## | 15: | DerivedAgeBracket10_clean | 0.008640294 |
| ## | 16: | City_catB | 0.008194383 |
| ## | 17: | HxlDxCoronaryAtherosclerosisAndOtherHeartDisease_clean | 0.007863241 |
| ## | 18: | Readmit360_clean | 0.007702091 |
| ## | 19: | ReligionCVDSC_lev_x. | 0.007316486 |
| ## | 20: | HxfSvcEmergencyMedicine_clean | 0.006811506 |
| ## | 21: | PrevDischargeDays_clean | 0.006342626 |
| ## | 22: | DerivedAgeOver65_clean | 0.006335854 |
| ## | 23: | HxbSvcEmergencyMedicine_clean | 0.006188493 |
| ## | 24: | LivingWillCVDSC_catB | 0.005707332 |
| ## | 25: | LivingWillCVDSC_lev_x.Unknown | 0.005592987 |
| ## | | variable | percentage |

Percutaneous Coronary Intervention (PCI)

| ## | | variable | percentage |
|---|---|---|---|
| ## | 1: | AgeInDays_clean | 0.067232734 |
| ## | 2: | DerivedAgeOver35_clean | 0.052521596 |
| ## | 3: | ReligionCVDSC_catB | 0.046277325 |
| ## | 4: | DerivedAgeOver50_clean | 0.045573961 |
| ## | 5: | DerivedAgeBracket10_clean | 0.030375991 |
| ## | 6: | DerivedAgeBracket5_clean | 0.028625588 |
| ## | 7: | SexCVDisplayDSC_lev_x.Male | 0.026755571 |
| ## | 8: | SexCVDisplayDSC_catB | 0.023538778 |
| ## | 9: | SexCVDisplayDSC_lev_x.Female | 0.020478790 |
| ## | 10: | City_catB | 0.018181907 |
| ## | 11: | DerivedAgeOver65_clean | 0.017654474 |
| ## | 12: | DerivedAgeBracket20_clean | 0.016734544 |
| ## | 13: | ReligionCVDSC_lev_x. | 0.016645654 |
| ## | 14: | ReligionCVDSC_lev_x.Unknown | 0.016426292 |
| ## | 15: | HxfSvcEmergencyMedicine_clean | 0.014750651 |
| ## | 16: | Zip_catB | 0.013958392 |
| ## | 17: | LivingWillCVDSC_catB | 0.013772811 |

-continued

| ## | | variable | percentage |
|---|---|---|---|
| ## | 18: | HxbSvcEmergencyMedicine_clean | 0.013460436 |
| ## | 19: | HxfDxCoronaryAtherosclerosisAndOtherHeartDisease_clean | 0.013022201 |
| ## | 20: | LivingWillCVDSC_lev_x.No . . . info.not.requested | 0.012739864 |
| ## | 21: | HxbRxThrombinInhibitors_clean | 0.010316149 |
| ## | 22: | HxbDxCoronaryAtherosclerosisAndOtherHeartDisease_clean | 0.009711793 |
| ## | 23: | LivingWillCVDSC_lev_x.Unknown | 0.008492407 |
| ## | 24: | MaritalTypeCVDSC_lev_x.Married | 0.007856852 |
| ## | 25: | MaritalTypeCVDSC_catB | 0.007732510 |
| ## | | variable | percentage |

Coronary Artery Bypass Grafting (CABG)

| # | | variable | percentage |
|---|---|---|---|
| ## | 1: | DerivedAgeOver35_clean | 0.038192552 |
| # | 2: | DerivedAgeOver50_clean | 0.034227483 |
| # | 3: | DerivedAgeBracket5_clean | 0.032881897 |
| # | 4: | AgeInDays_clean | 0.024806579 |
| # | 5: | HxlRxAngiotensinConvertingEnzymeAceInhibitors_clean | 0.023433258 |
| # | 6: | PrevDischargeDaysAvg_clean | 0.019260775 |
| # | 7: | HxbSxCvLhcPoss_clean | 0.018411608 |
| # | 8: | DerivedAgeOver65_clean | 0.017517914 |
| # | 9: | City_catB | 0.014399556 |
| # | 10: | DerivedAgeBracket10_clean | 0.014203597 |
| # | 11: | Zip_catB | 0.013836036 |
| # | 12: | PrevDischargeDays_clean | 0.013716944 |
| # | 13: | SexCVDisplayDSC_lev_x.Female | 0.013642128 |
| # | 14: | SexCVDisplayDSC_lev_x.Male | 0.012971443 |
| # | 15: | HxlDxDiabetesMellitusWithComplications_clean | 0.012129624 |
| # | 16: | SexCVDisplayDSC_catB | 0.011755173 |
| # | 17: | HxfDxResidualCodesUnclassified_clean | 0.010538152 |
| # | 18: | HxlRxInsulin_clean | 0.010174556 |
| # | 19: | PrevDischargeHourOfDay_clean | 0.009811546 |
| # | 20: | HxfDxDiabetesMellitusWithoutComplication_clean | 0.009714577 |
| # | 21: | HxbRxHeparinAntagonists_clean | 0.009660813 |
| # | 22: | LivingWillCVDSC_catB | 0.009389412 |
| # | 23: | HxfSvcEmergencyMedicine_clean | 0.009372530 |
| # | 24: | HxfRxLaxatives_clean | 0.009130582 |
| # | 25: | HxfRxBenzodiazepines_clean | 0.008906585 |
| ## | | variable | percentage |

40

Death

| ## | | variable | percentage |
|---|---|---|---|
| ## | 1: | DerivedAgeOver50_clean | 0.145058791 |
| ## | 2: | DerivedAgeOver35_clean | 0.123871441 |
| ## | 3: | DerivedAgeOver65_clean | 0.122614082 |
| ## | 4: | HxbDxSecondaryMalignancies_clean | 0.037246707 |
| ## | 5: | LivingWillCVDSC_catB | 0.030474267 |
| ## | 6: | AgeInDays_clean | 0.029054825 |
| ## | 7: | DerivedAgeBracket20_clean | 0.028141903 |
| ## | 8: | PrevDischargeDispositionCVDSC_catB | 0.026751671 |
| ## | 9: | PrevExcessIP30_clean | 0.023680166 |
| ## | 10: | PrevExcess30_clean | 0.015673708 |
| ## | 11: | ReligionCVDSC_lev_x.Unknown | 0.014915092 |
| ## | 12: | ReligionCVDSC_catB | 0.012016431 |
| ## | 13: | HxfSvcEmergencyMedicine_clean | 0.011180913 |
| ## | 14: | PrevDischargeSkilledNursing_clean | 0.009617624 |
| ## | 15: | ReferringFacilityCVDSC_catB | 0.008745688 |
| ## | 16: | PrevExcessED30_clean | 0.008321500 |
| ## | 17: | LivingWillCVDSC_lev_x.Unknown | 0.007671592 |
| ## | 18: | Zip_catB | 0.006869059 |
| ## | 19: | ReferringFacilityCVDSC_lev_x. | 0.006784275 |
| ## | 20: | MeanPrevLengthOfStayDays_clean | 0.006687735 |
| ## | 21: | HxlDxRespiratoryFailureInsufficiencyArrestAdult_clean | 0.006561566 |

| ## | | variable percentage |
|---|---|---|
| ## 22: | DerivedAgeBracket5_clean | 0.006371687 |
| ## 23: | City_catB | 0.006181310 |
| ## 24: | DerivedAgeOver80_clean | 0.004843680 |
| ## 25: | LivingWillCVDSC_lev_x. | 0.004593015 |
| ## | | variable percentage |

Furthermore, some analytic results data may require use of both historical/chronological and current (such as real time or near real time relative to entry at an EMR system) data.

Additionally, some forms of analytic results data may require analysis using EMR data relating to many different patients, transactions, or events.

FIG. 6 illustrates a screenshot of an exemplary user interface display according to some embodiments of the invention. The user interface dashboard 600 is generally designed to be available to clinicians in the ED, and in some embodiments of the present invention, comprise a table having a number of rows and columns, where each row corresponds to one patient in the ED. The user interface dashboard 600 is updated in real time or near real time. Patients presenting in the ED with unspecified chest pain may have their cardiac predictive risk estimate displayed in column 610, and their predicted outcome in column 620. Other patent applications describe in detail exemplary embodiments of this and other user interface displays according to some embodiments of the invention, including but not limited to, co-pending U.S. patent application Ser. No. 16/378,439, filed on Apr. 8, 2019, and Ser. No. 16/378, 542, filed on Apr. 8, 2019, which is herein incorporated by reference in its entirety.

Figure 7:
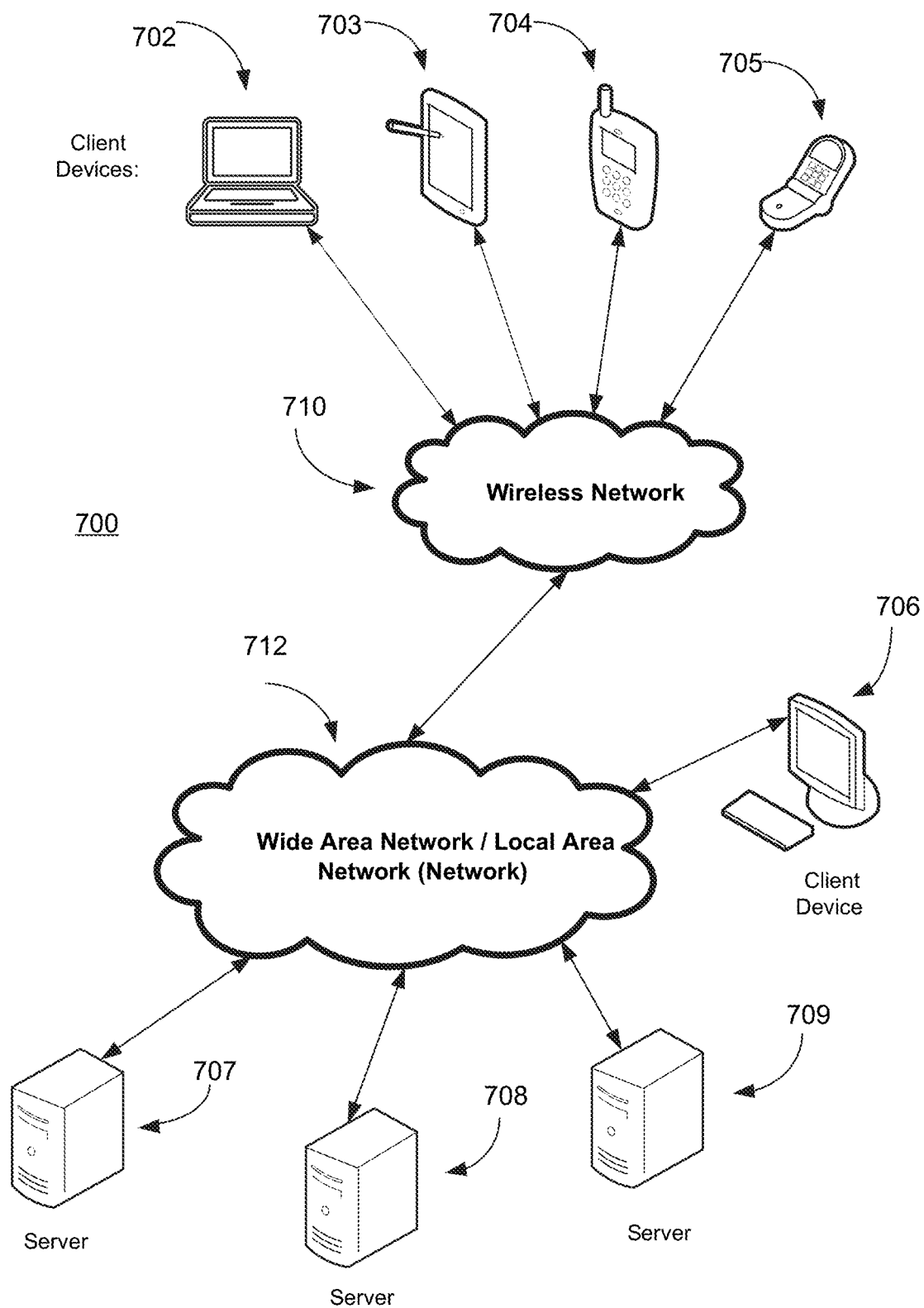
FIG. 7 illustrates a block diagram of a distributed computer system that can implement one or more aspects of an embodiment of the invention.

FIG. 7 illustrates components of one embodiment of an environment 700 in which the invention may be practiced. Not all of the components may be required to practice the invention, and variations in the arrangement and type of the components may be made without departing from the spirit or scope of the invention. As shown, the system 700 includes one or more Local Area Networks ("LANs")/Wide Area Networks ("WANs") 712, one or more wireless networks 710, one or more wired or wireless client devices 706, mobile or other wireless client devices 702-706, servers 707-709, and may include or communicate with one or more data stores or databases. Various of the client devices 702-706 may include, for example, desktop computers, laptop computers, set top boxes, tablets, monitors, cell phones, smart phones, devices for interfacing with, or viewing dashboards or analytics relating to, EMR related systems or entities, etc. The servers 707-709 can include, for example, one or more application servers, content servers, search servers, Mirth or other HL7 Messaging servers, Database servers, database management or SQL servers, other servers relating to EMR related systems, etc.

Figure 8:
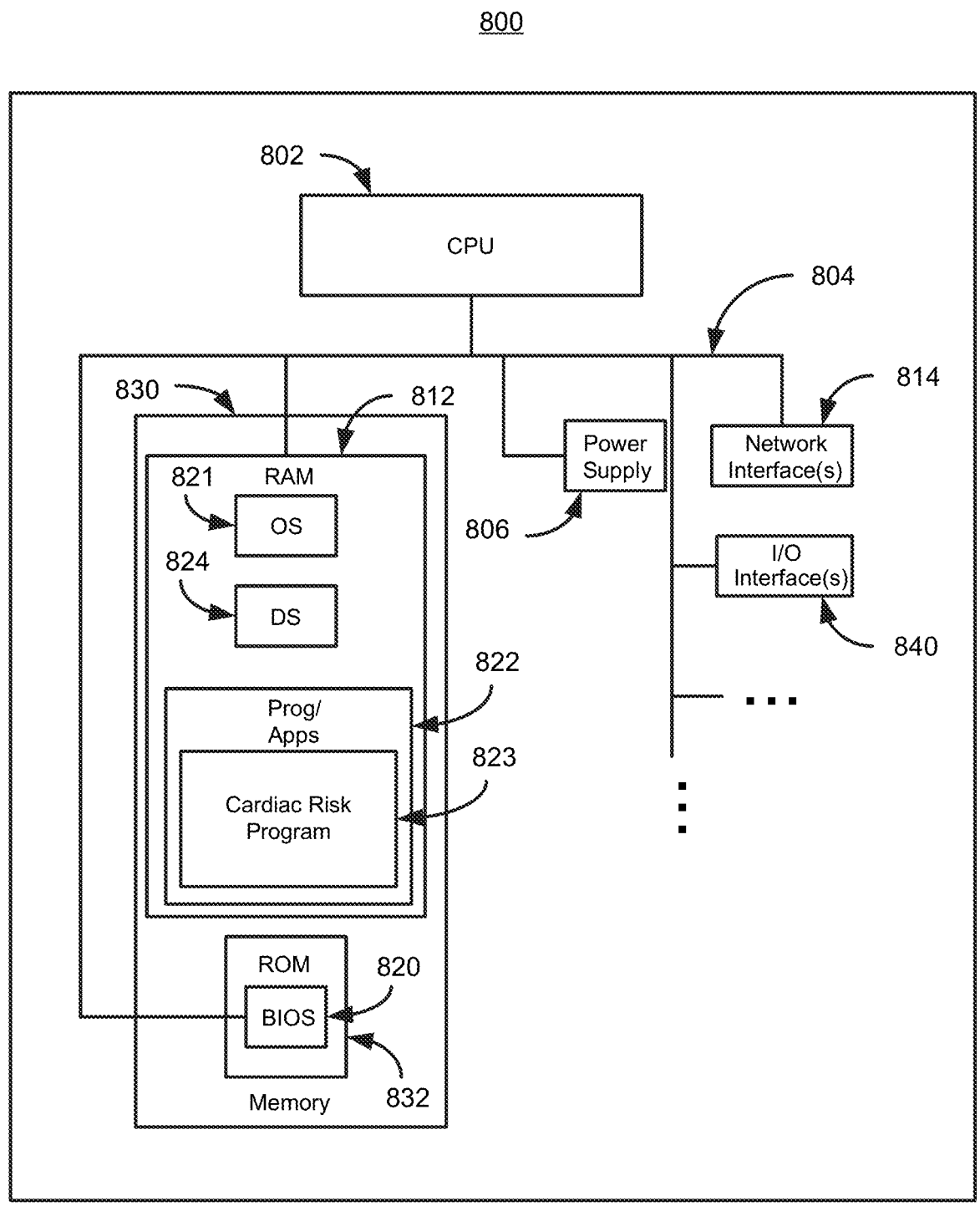
FIG. 8 illustrates a block diagram of an electronic device that can implement one or more aspects of an embodiment of the invention.

FIG. 8 illustrates a block diagram of an electronic device 800 that can implement one or more aspects of EMR related systems and methods according to embodiments of the invention. Instances of the electronic device 800 may include servers, e.g., servers 707-709, and client devices, e.g., client devices 702-706. In general, the electronic device 800 can include a processor/CPU 802, memory 830, a power supply 806, and input/output (I/O) components/devices 840, e.g., microphones, speakers, displays, touchscreens, keyboards, mice, keypads, microscopes, GPS components, etc., which may be operable, for example, to provide graphical user interfaces, dashboards, etc.

A user may provide input via a touchscreen of an electronic device 800. A touchscreen may determine whether a user is providing input by, for example, determining whether the user is touching the touchscreen with a part of the user's body such as his or her fingers. The electronic device 800 can also include a communications bus 804 that connects the aforementioned elements of the electronic device 800. Network interfaces 814 can include a receiver and a transmitter (or transceiver), and one or more antennas for wireless communications.

The processor 802 can include one or more of any type of processing device, e.g., a Central Processing Unit (CPU), and a Graphics Processing Unit (GPU). Also, for example, the processor can be central processing logic, or other logic, may include hardware, firmware, software, or combinations thereof, to perform one or more functions or actions, or to cause one or more functions or actions from one or more other components. Also, based on a desired application or need, central processing logic, or other logic, may include, for example, a software-controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software.

The memory 830, which can include Random Access Memory (RAM) 812 and Read Only Memory (ROM) 832, can be enabled by one or more of any type of memory device, e.g., a primary (directly accessible by the CPU) or secondary (indirectly accessible by the CPU) storage device (e.g., flash memory, magnetic disk, optical disk, and the like). The ROM 832 can also include Basic Input/Output System (BIOS) 820 of the electronic device.

The RAM can include an operating system 821, data storage 824, which may include one or more databases, and programs and/or applications 822 and a cardiac risk program 823. The cardiac risk program 823 is intended to broadly include all programming, applications, algorithms, software and other and tools necessary to implement or facilitate methods and systems according to embodiments of the invention. Elements of the cardiac risk program 823 program may exist on a single server computer or be distributed among multiple computers, servers, devices or entities, or sites.

The power supply 806 contains one or more power components and facilitates supply and management of power to the electronic device 800.

The input/output components, including Input/Output (I/O) interfaces 840, can include, for example, any interfaces for facilitating communication between any components of the electronic device 800, components of external devices (e.g., components of other devices of the network or system 800), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 840 and the bus 804 can facilitate communication between components of the electronic device 800, and in an example can ease processing performed by the processor 802.

Where the electronic device 800 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications.

Any computing device capable of sending, receiving, and processing data over a wired and/or a wireless network may act as a server, such as in facilitating aspects of implementations of EMR and cardiac risk related systems and methods according to embodiments of the invention. Devices acting as a server may include devices such as dedicated rack-mounted servers, desktop computers, laptop computers, set top boxes, integrated devices combining one or more of the preceding devices, etc.

Servers may vary widely in configuration and capabilities, but they generally include one or more central processing units, memory, mass data storage, a power supply, wired or wireless network interfaces, input/output interfaces, and an operating system such as Windows® Server, macOS®, Unix®, Linux®, FreeBSD, and the like.

A server may include, for example, a device that is configured, or includes a configuration, to provide data or content via one or more networks to another device, such as in facilitating aspects of an example EMR systems and methods according to embodiments of the invention. One or more servers may, for example, be used in hosting a Web site, such as the web site microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of EMR systems and methods according to embodiments of the invention. Content may include, for example, text, images, audio, video, and the like.

In example aspects of EMR systems and methods according to embodiments of the invention, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, monitors, sensor-equipped devices, laptop computers, set top boxes, wearable computers, integrated devices combining one or more of the preceding devices, and the like.

Client devices may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, GPS or other location-aware capability, and a 2D or 3D touch-sensitive color screen on which both text and graphics may be displayed.

Client devices, such as client devices 702-706, for example, as may be used in example EMR systems and methods according to embodiments of the invention, may run a variety of operating systems, including personal computer operating systems such as Windows®, iOS®, or Linux®, and mobile operating systems such as iOS®, Android®, Windows Mobile®, and the like. Client devices may be used to run one or more applications that are configured to send or receive data from another computing device. Client applications may provide and receive textual content, multimedia information, and the like. Client applications may perform actions such as viewing or interacting with analytics or dashboards, interacting with medical, patient-related, hospital or medical facility-related, EMR or EMR-related entities or systems, browsing webpages, using a web search engine, interacting with various apps stored on a smart phone, sending and receiving messages via email, SMS, or MMS, playing games, receiving advertising, watching locally stored or streamed video, or participating in social networks.

In example aspects of EMR systems and methods according to embodiments of the invention, one or more networks, such as networks 710 or 712, for example, may couple servers and client devices with other computing devices, including through wireless network to client devices. A network may be enabled to employ any form of computer readable media for communicating information from one electronic device to another. A network may include the Internet in addition to Local Area Networks (LANs), Wide Area Networks (WANs), direct connections, such as through a Universal Serial Bus (USB) port, other forms of computer-readable media, or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 710, as in example EMR systems and methods according to embodiments of the invention, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long-haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in example EMR systems and methods according to embodiments of the invention, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's Web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

One embodiment of the present invention includes systems, methods, and a non-transitory computer readable storage medium or media tangibly storing computer program logic capable of being executed by a computer processor.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the appended claims.

APPENDIX

```
denormalize <- function(x=NULL,mapping=NULL,nthreads=NULL){
    # safety ----------------------------------------------------------------
    ----------
    # data input
    stopifnot(!is.null(x))
    stopifnot(is.data.frame(x))
    if(!"data.table" %in% class(x))
        data.table::setDT(x)
    stopifnot("encounter" %in% names(x))      # 1 row per observation
    stopifnot("person" %in% names(x))         # follows across time
    stopifnot("catagory" %in% names(x))       # will eventually map to a column
    stopifnot("ds" %in% names(x))             # following prophet function input
    # function input
    stopifnot(!is.null(mapping))
    stopifnot(!is.function(mapping))
    #nthreadinput
    if(!is.null(nthreads)){
        stopifnot(nthreads <= parallel::detectCores( ))
    }
    # data preparation ------------------------------------------------------
    --------
    # column of 1's for casting
    x[, cast := 1]
```

```
# map categories to safe names
# a default is provided, but it could be any lookup
x[, category := mapping(category)]
# dates are sanitary?
datestamps <- as.POSIXct(x[["ds"]])
if(sum(is.na(datestamps)) > 0){
    warning("EXCEPTION when coverting to POSIXct, returning problematic rows")
    return(x[is.na(datestamps),])
}
x[,ds := datestamps] # overwrite with POSIXxt class
rm(datestamps)
# people are sanitary
people <- x[["person"]]
if(sum(is.na(people)) > 0){
    warning("EXCEPTION with null people, returning problematic rows")
    return(x[is.na(people),])
}
rm(people)
# encounters are sanitary
encounter <- x[["encounter"]]
if(sum(is.na(encounter)) > 0){
    warning("EXCEPTION with null, encounters, returning problematic rows")
    return(x[is.na(encounter),])
}
rm(encounter)
# anonymous function for parallelization -------------------------------------
execution <- function(x){
    cummax.na <- function(x) {
        y <- copy(x)
        x[which(is.na(x))] <- 0
        out <- cummax(x)
        out[is.na(y)] <- NA
        return(out)
    }
    # cast to binary ---------------------------------------------------------
    pop <- x[,list(
        start = min(ds),
        end = max(ds)
    ),
    by=c("encounter","person")
    ]
    # binary indicator column, if t
    wide <- data.table::dcast(
        data = x,
        formula = encounter ~ category,
        value.var = "cast",
        fun.aggregate = max,
        fill = 0
    )
    features <- setdiff(names(wide),"encounter")
    # join in lookup information
    data.tables::setkey(wide, "encounter")
    data.table::setkey(pop, "encounter")
    wide <- merge(wide,pop) # inner join, by definition they all overlap
    data.table::setcolorder(wide,c("encounter", "person", "start", "end", features))
    wide <- wide[order(person,start),]
    # engineering across time ------------------------------------------------
    # get the order right
    data.table::setkey(wide,"person", "start")
    # does the patient have a binary history
    history <- copy(wide)
    for(f in seq_along(features)){
        history[,eval(features[f]) := shift(get(features[f]),n=1L,type="lag"),by=c("person")]
        history[,eval(features[f]) := cummax.na(get(features[f])),by=c("person")]
    }
    # first and last days ----------------------------------------------------
    lookup <- melt(
        history,
        id.cols.=c("encounter","person","start","end"),
        measurs.vars = features
    )[value==1,] #only keep those rows with medical history
    # Lookup[is.na(value),value := 0]
```

```
    names(lookup)
    lookup[,value := NULL]
    # get the right order
    setkey(lookup,"person","category","start")
    # calculate the dates
    lookup[,first := min(start),by=c("person","category")]
    lookup[,last := shift(start,n=1L,type="lag"),by=c("person","category")]
    # difference the days
    lookup[,first_days := as.numeric(difftime(start,first,units="days"))]
    lookup[,last_days := as.numeric(difftime(start,last,units="days"))]
    # cast to wide
    first_days <- data.table::dcast(
       data = lookup,
       formula = encounter ~ category,
       value.var = "first_days",
       fun.aggregate = max,
       fill = 0
    )
    data.table::setnames(
       first_days,
       names(first_days),
       c("encounter",paste0("HxFirst",names(first_days)[2:ncol(first_days)]))
    )
    # cast to wide
    last_days <- data.table::dcast(
       data = lookup,
       formula = encounter ~ category,
       value.var = "last_day",
       fun.aggregate = max,
       fill = 0
    )
    data.table::setnames(
       last_days,
       names(last_days),
       c("encounter",paste0("HxLast",names(last_days)[2:ncol(last_days)]))
    )
    data.table::setnames(
       wide,
       names(wide),
       c("encounter","person","start","end",paste0("HxBinary",names(wide)[5:cnol
(wide)]))
    )
    # merge 3 wide tables
    names(history)[5:ncol(history)] <- paste0("HxBinary",names(history)[5:nco1
(history)])
    data.table::setkey(history,"encounter")
    data.table::setkey(first_days,"encounter")
    data.table::setkey(last_days,"encounter")
    return(
       Reduce(
          function(x,y) merge(x,y,all.x=TRUE),
          list(
             history,
             first_days,
             last_days
          )
       )
    )
 }
 # execute based on parallel request - - - - - - - - - - - - - - - - - - - - - - - - - - - - - - - - - - - - - - -
- - -
 # single thread
 if(is.null(nthreads)){
    out <- execution(x)
 # other multithreaded
 } else {
    # functions to safely manage parallel backend
    print("Parallel Execution Requsted")
    c1 <- NULL
    shutdown <- function(c1= NULL) {
       # shut down in cluster present
       if (class(c1)
          parallel::stopCluster(c1)
          c1 <- NULL
       }
       return(NULL)
    }
    on.exit(c1 <- shutdown(c1))
    cl <- parallel::makeCluster(nthreads)
```

```
# parallelize so each chunk has all rows for 1 person
parallel::clusterEvalQ(cl,library(data.table))
observations <- split(x,as.factor(x$person))
out <- data.table::rbindlist(
   parallel::parLapply(
      cl = cl,
      X = observations,
      fun = execution
   ),
   fill = TRUE
)
}
# impute with 0
# chunks all missing to 1 end of distribution
history <- names(out)[grepl("Hx",names(out))]
for(h in seq_along(history)){
   data.table::set(
      out,
      i = which(is.na(out[[history[h]]])),
      j = history[h],
      value = 0
   )
}
return(out[order(person,start)])
}
```

What is claimed is:

1. A method for estimating, in real-time or near-real-time, a risk of acute myocardial infarctions in at least one patient, wherein the at least one patient is in a current medical encounter with at least one clinician in a medical facility, the method comprising:

extracting batch information at a pre-defined time interval for one or more past patients from an electronic medical records (EMR) database into a batch database operably connected to a machine learning model comprising one or more medical feature coefficients obtained from training the machine learning model;

calculating, using the machine learning model, a risk level for the one or more past patients in the batch database, wherein the one or more past patients includes the at least one patient, and the risk level for the at least one patient is calculated using one or more medical feature coefficients obtained from the machine learning model;

storing the calculated risk level in the batch database;

constructing a real-time database from streams of real-time Health Level 7 (HL7) clinical administrative data, wherein at least one stream of real-time HL7 clinical administrative data is associated with the at least one patient in a current medical encounter, the at least one stream of real-time HL7 clinical administrative data is received in real-time or near real-time relative to entry of EMR data into an EMR system, and the at least one stream of real-time HL7 clinical administrative data is parsed in real-time or near real-time to identify and extract specified EMR data comprising patient clinical data obtained during the current medical encounter into the real-time database, the patient clinical data comprising one or more of a health-related patient complaint, a lab test order for diagnosing a medical condition, and patient vital data for the at least one patient;

predicting, in real-time or near-real-time, the risk of acute myocardial infarction in the at least one patient in a current medical encounter, wherein a real-time risk prediction value is estimated by adjusting the calculated risk level for the at least one patient by applying a linear model, different from the machine learning model, to one or more of the medical feature coefficients obtained from the machine learning model and to the specified real-time EMR data from the at least one patient; and displaying a risk prediction of acute myocardial infarction in the at least one patient on a user interface of a device for presentation to the at least one clinician wherein the risk prediction is based on the real-time risk prediction value and comprises a recommendation to admit or discharge the at least one patient into or from the medical facility.

2. The method of claim 1, wherein the one or more past patients includes the at least one patient in a current medical encounter.

3. The method of claim 1, wherein the at least one patient in a current medical encounter is a new patient.

4. The method of claim 1, further comprising storing the risk prediction value in the real-time database.

5. The method of claim 1, wherein the real-time database further comprises one or more derived medical features of a real-time patient encounter.

6. The method of claim 1, wherein the machine learning model comprises a gradient boosting machine.

7. The method of claim 1, wherein the pre-defined time interval comprises 24 hours.

8. A system for estimating, in real-time or near-real-time, a risk of acute coronary syndrome in at least one patient, wherein the at least one patient is in a current medical encounter with at least one clinician in a medical facility, the system comprising:

at least one health system server comprising at least one electronic medical records (EMR) database;

a plurality of data servers comprising:

at least one batch server comprising one or more batch databases, extracting updated batch information at a pre-defined time interval for one or more past patients from the electronic medical records (EMR) database into a batch database operably connected to a machine learning model comprising one or more medical feature coefficients obtained from training the machine learning model, and at least one real-time server comprising one or more real-time databases, receiving streams of real-time or near real-time Health Level 7 (HL7) clinical administrative data, wherein at least one stream of real-time HL7 clinical administrative data is associated with the at least one patient in a current medical encounter, wherein the at least one stream of real-time HL7 clinical administrative data is received in real-time or near real-time relative to entry of EMR data into an EMR system, and the at least one stream of real-time HL7 clinical administrative data is parsed in real-time or near real-time to identify and extract specified EMR data comprising patient clinical data obtained during the current medical encounter, the patient clinical data comprising one or more of a health-related patient complaint, a lab test order for diagnosing a medical condition, and patient vital data;

a modeling server calculating a risk level for the one or more past patients in the batch database using the machine learning model wherein the one or more past patients includes the at least one patient, and the risk level for the one or more past patients is calculated using one or more medical feature coefficients obtained from the machine learning model, and predicting, in real-time or near-real-time, the risk of acute coronary syndrome in the at least one patient in a current medical encounter, wherein a risk prediction value is estimated by applying a linear model, different from the machine learning model, to one or more of the medical feature coefficients obtained from the machine learning model and to the specified real-time EMR data, to adjust the calculated risk level for the at least one patient; and a business integration server configuring and transmitting a display of the risk prediction of acute coronary syndrome in the at least one patient on a user interface of a device for presentation to the at least one clinician wherein the risk prediction is based on the risk prediction value and comprises a recommendation to admit or discharge the at least one patient into or from the medical facility.

9. The system of claim 8, wherein the one or more past patients includes the at least one patient in a current medical encounter.

10. The system of claim 8, wherein the at least one patient in a current medical encounter is a new patient.

11. The system of claim 8, wherein the risk prediction value is stored in the one or more real-time databases.

12. The system of claim 8, wherein the one or more real-time databases comprise one or more derived features of a real-time patient encounter.

13. The system of claim 8, wherein the machine learning model comprises a gradient boosting machine.

14. The system of claim 8, wherein the pre-defined time interval comprises 24 hours.

15. A computer related product comprising a non-transitory computer readable medium storing instructions for estimating, in real-time or near-real-time, a risk of acute myocardial infarction in at least one patient, wherein the at least one patient is in a current medical encounter with at least one clinician in a medical facility, wherein the instructions upon execution by a processor perform the steps of:

extracting updated batch information at a pre-defined time interval for one or more past patients from an electronic medical records database into a batch database operably connected to a machine learning model comprising one or more medical feature coefficients obtained from training the machine learning model;

calculating, using the machine learning model, a risk level for the one or more past patients in the batch database wherein the one or more past patients includes the at least one patient, and the risk level for the at least one patient is calculated using one or more medical feature coefficients obtained from the machine learning model;

storing the calculated risk level in the batch database;

constructing a real-time database from streams of real-time Health Level 7 (HL7) clinical administrative data, wherein at least one stream of real-time HL7 clinical administrative data is associated with the at least one patient in a current medical encounter, the at least one stream of real-time HL7 clinical administrative data is received in real-time or near real-time relative to entry of EMR data into an EMR system, and the at least one stream of real-time HL7 clinical administrative data is parsed in real-time or near real-time to identify and extract specified EMR data comprising patient clinical data obtained during the current medical encounter, the patient clinical data comprising one or more of a health-related patient complaint, a lab test order for diagnosing a medical condition, and patient vital data;

predicting, in real-time or near-real-time, the risk of acute myocardial infarction in the at least one patient in a current medical encounter, wherein a real-time risk prediction value is estimated by adjusting the calculated risk level for the at least one patient by applying a linear model, different from the machine learning model, to one or more of the medical feature coefficients obtained from the machine learning model and to the specified EMR data from the at least one patient; and displaying a risk prediction of acute myocardial infarction in the at least one patient on a user interface of a device for presentation to the at least one clinician wherein the risk prediction is based on the real-time risk prediction value and comprises a recommendation to admit or discharge the at least one patient into or from the medical facility.

16. The computer related product of claim 15, wherein the one or more past patients includes the at least one patient in a current medical encounter.

17. The computer related product of claim 15, wherein the at least one patient in a current medical encounter is a new patient.

18. The computer related product of claim 15, wherein the instructions upon execution by a processor further perform the step of storing the real-time risk prediction value in the real-time database.

19. The computer related product of claim 15, wherein the real-time database further comprises one or more derived features of a real-time patient encounter.

20. The computer related product of claim 15, wherein the machine learning model comprises a gradient boosting machine.

21. The computer related product of claim 15, wherein the pre-defined time interval comprises 24 hours.

* * * * *